(12) United States Patent
Utecht et al.

(10) Patent No.: US 8,546,384 B2
(45) Date of Patent: *Oct. 1, 2013

(54) BONDING TISSUES AND CROSS-LINKING PROTEINS WITH NAPHTHALIMIDE COMPOUNDS

(75) Inventors: Ronald E. Utecht, Volga, SD (US);
Kaia L. Kloster, Hudson, SD (US);
Millard M. Judy, Redmond, WA (US);
Kevin J. Vaska, Sioux Falls, SD (US);
James L. Matthews, Dallas, TX (US)

(73) Assignee: Alumend, LLC, Sioux Falls, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,196

(22) Filed: Jul. 12, 2012

(65) Prior Publication Data

US 2013/0045171 A1  Feb. 21, 2013

Related U.S. Application Data

(62) Division of application No. 12/407,481, filed on Mar. 19, 2009, now Pat. No. 8,242,114, which is a division of application No. 10/982,197, filed on Nov. 5, 2004, now Pat. No. 7,514,399.

(60) Provisional application No. 60/517,618, filed on Nov. 5, 2003.

(51) Int. Cl.
*A61K 31/535* (2006.01)

(52) U.S. Cl.
USPC ..................................... 514/229.5

(58) Field of Classification Search
None
See application file for complete search history.

(56) References Cited

U.S. PATENT DOCUMENTS

| 5,235,045 | A | 8/1993 | Lewis et al. |
| 5,565,551 | A | 10/1996 | Lewis et al. |
| 5,766,600 | A | 6/1998 | Lewis et al. |
| 5,917,045 | A | 6/1999 | Lewis et al. |
| 5,986,043 | A | 11/1999 | Hubbell et al. |
| 6,306,922 | B1 | 10/2001 | Hubbell et al. |
| 6,410,505 | B1 | 6/2002 | Lewis et al. |
| 7,514,399 | B2 * | 4/2009 | Utecht et al. .................. 514/1.1 |
| 8,242,114 | B2 * | 8/2012 | Utecht et al. ............... 514/229.5 |
| 2009/0181927 | A1 * | 7/2009 | Utech et al. ..................... 514/56 |

FOREIGN PATENT DOCUMENTS

| EP | 0 187 076 A1 | 7/1986 |
| WO | WO 90/04394 A1 | 5/1990 |
| WO | WO 01/17356 A1 | 3/2001 |
| WO | WO 03/072058 A2 | 9/2003 |

OTHER PUBLICATIONS

Leveen, R., et al., "New Rabbit Atherosclerosis Model for the Investigation of Transluminal Angioplasty", Investigative Radiology, 1982, vol. 17, pp. 470-475.

IEuropean Search Report, European Patent Office, Mar. 16, 2009.

* cited by examiner

*Primary Examiner* — Marcela M Cordero Garcia
(74) *Attorney, Agent, or Firm* — Novak Druce Connolly Bove + Quigg LLP

(57) ABSTRACT

Naphthalimide compounds are used in tissue bonding and protein cross-linking applications. When activated by an activating agent, such as light in the 400-500 nm absorption range, the naphthalimide compounds form chemically-reactive species that cross-link proteins, bond connective tissues together, and bond tissues and other biomaterials together. A naphthalimide-labeled biomolecule, such as a naphthalimide-labeled chitosan, is also capable of bonding tissues without subsequent direct illumination of the contacted tissue area. The naphthalimide compounds may be used in tissue or arterial repair, stabilization of an expanded arterial wall after angioplasty, tethering pharmaceutical agents to tissue surfaces to provide local drug delivery, and for chemically bonding skin care products, sunscreens, and cosmetics to the skin.

7 Claims, 24 Drawing Sheets

BONDING TISSUES AND CROSS-LINKING PROTEINS WITH NAPHTHALIMIDE COMPOUNDS

This application claims priority to U.S. patent application Ser. No. 12/407,481, filed on Mar. 19, 2009, now U.S. Pat. No. 8,242,114, issued on Aug. 14, 2012; U.S. Pat. No. 7,514,399, issued on Apr. 7, 2009; and U.S. Provisional Patent Application Ser. No. 60/517,618, entitled "BONDING TISSUES AND CROSS-LINKING PROTEINS WITH NAPHTHALIMIDE COMPOUNDS" filed on Nov. 5, 2003, having Ronald E. Utecht, Kaia L. Kloster, Millard M. Judy, Kevin J. Vaska, and James L. Matthews, listed as the inventor(s), the entire contents of which is are hereby incorporated by reference.

BACKGROUND

This invention relates to naphthalimide compounds and their use in tissue bonding and protein cross-linking. This invention also pertains to devices and methods for arterial repair, preservation of expanded internal luminal diameters, and local delivery of drugs, skin care materials, sunscreens, and cosmetics.

Wound closure in body tissues while maintaining low levels of inflammation with resulting granuloma formation and attaining patency against leakage across the walls of luminal structures such as blood vessels remains a significant problem in surgical and trauma practice. Current closure practices involving sutures or mechanical devices such as clips, staples, or nails result in the introduction of foreign materials, which are sources of foreign body reactions and inflammation, and the formation of holes through luminal walls by the closing agent, which serve as potential avenues of post-operative fluid leakage and loss of luminal patency.

From catgut to synthetic polymers, sutures have been the traditional tool for vascular repair. However, fistulas and granulomas can form as a result of intolerance to the suture material. Suture techniques can also result in smaller residual lumens and reduced perfusion. These side effects can lead to necrosis, healing disorders, and ultimate dehiscence of the wound. Furthermore, leakage from the needle puncture sites can be problematic, particularly in cerebral applications or in patients with a compromised ability to achieve hemostasis (i.e. hemophiliacs or patients undergoing anticoagulant therapy). Finally, suture techniques are tedious and time-consuming, requiring a concerted effort on the part of the surgeon and therefore contributing to overall expense.

Mechanical assists such as staples and vascular clips have been proposed to facilitate tissue repair. While they do shorten operative times, the associated expense and potential risk of clip failure raise questions regarding their benefits over sutures. Furthermore, some staples require removal and may be associated with more patient discomfort.

Laser thermal tissue welding experiments report mixed results in achieving tissue bonds. Numerous infrared wavelengths, including those of the Nd:YAG, Argon, and $CO_2$ lasers, have been tried. Laser welding has proven to be an exacting methodology, where insufficient exposures result in ineffective tissue bonding and high temperatures are associated with tissue destruction. In fact, the requisite denaturation of proteins (with tissue temperatures in the range of 60-80° C.) and associated collateral thermal damage appear to be the primary limiting factors for this technique.

Inflammation arising from foreign-material based wound closing agents can result, for example, in sufficient scarring to seriously impede function such as by imposing a barrier to laminar blood flow in a blood vessel possibly leading to clot formation and subsequent complications, or by degrading the desired cosmetic effects in skin plastic or trauma repair surgery.

Tissue adhesives comprising protein species, synthetic polymers, and biological materials have been advocated for wound repair to eliminate or minimize mechanical or foreign body effects. Protein based systems such as fibrin solutions and sprays offer hemostasis but little in the way of mechanical strength in holding opposing surfaces together. Synthetic polymeric glues such as polylactates and polyglycolates offer mechanical strength, but their products of chemical attachment in tissue are toxic and inflammatory. Acrylic based cements offer strength but are confined to external use on skin wounds because they are toxic and as a film impede migration of molecular and cellular species across bonded surfaces. Tissue adhesives incorporating aldehyde based protein cross-linking agents such as BioGlue™ have been used. However, long term diffusion of the aldehyde species away from the binding site leads to deleterious inflammation and granuloma formation.

The concept of a "patch" is also known. Various vascular repair procedures, notably carotid endarterectomy closure, have utilized numerous patch materials. It is important to note that this type of patching requires tailored fitting and extensive suturing to repair the site of injury. However, there are some associated benefits. The use of a patch helps avoid residual stenosis and decreases the likelihood of restenosis. Furthermore, a patch makes for easier closure under these difficult conditions and suffers less perioperative thrombosis. The size and shape of the patch are important to long-term success. A patch that is too large can lead to increases in wall stress and ultimate dilation or rupture. Large deviations from the native lumen size can also lead to increases in turbulence in blood flow, often associated with low shear rates and progression of the atherosclerotic process in arteries that are so predisposed. Experience would suggest that a long, tapered, panhandle shaped patch serves better than an oval patch to maximize the benefits and avoid potential risks.

What is needed is a method of applying a patch over an arterial lesion which achieves structural competency and hemostasis without attendant leakage of blood through the luminal wall and patch, granulomatous tissue growth into the vessel lumen, decrease in luminal area due to foreign body reaction, and initiation of intraluminal clot formation.

Prior tissue bonding technology using 4-amino-1,8-naphthalimide biomolecular cross-linking has successfully achieved tissue closure without inflammatory reactions or penetration by foreign objects. (U.S. Pat. Nos. 5,235,045; 5,565,551; 5,766,600; 5,917,045; and 6,410,505; the content of each of these patents is incorporated by reference herein). This tissue bonding technology requires the application of light having a wavelength within the absorption spectrum of 400-500 nm (blue light) to the photochemical upon the tissue or biomaterial surfaces in order to initiate the photochemical bonding process. Minimization of light requirements would facilitate the ease of use for clinicians.

What is also needed, therefore, is a means of attaching two tissue surfaces together or a tissue surface to a compatible biomaterial to effect wound closure that does not introduce a material that induces an inflammatory reaction or compromise the structural integrity of a luminal wall. What is further needed is a means of attaching two tissue surfaces or a tissue surface and a compatible biomaterial that does not require direct application of light to the tissue surfaces being attached.

Concerns also exist for the long-term retention of the opened arterial lumen after balloon dilation during percutaneous transluminal coronary angioplasty ("PTCA"), which is limited by processes that lead to re-occlusion within 3-6 months. PTCA has been one of the primary treatment modalities for revascularization of arterial stenoses. However, two aspects of PTCA have motivated cardiologists to seek alternative methods of treating the coronary stenosis: (1) acute ischemic complications related to vessel injury and the PTCA procedure itself, and (2) the occurrence of late restenosis, or reclosure of the treated site.

The occurrence of restenosis, or reclosure of the dilated vessel within 3-6 months of treatment, is the primary problem arising from the PTCA treatment and appears to be related to vascular injury. Damage to the vessel wall can lead to the release of thrombogenic, chemotactic, and growth factors. Endothelial denudation promotes platelet aggregation, thrombus formation, and activation of macrophages, lymphocytes, and smooth muscle cells. Activated platelets proceed to release additional mitogens including platelet derived growth factor ("PDGF"), fibroblast growth factor ("FGF"), and epidermal growth factor ("EGF"). Another contributing factor to loss of luminal diameter is the passive process of elastic recoil. The elastic nature of the vasculature promotes return to its original dimensions and can account for a significant loss of initial diameter gain. The excessive reparative response, compounded by elastic recoil, can become occlusive in itself propagating symptomatic recurrence including myocardial ischemia and angina. Alterations in local rheology such as turbulence and elevated shear stresses have also been associated with the restenosis process.

A significant decrease in numbers and rates of re-occlusion has been obtained by use of a mechanical cylindrically-shaped device, a stent, which maintains the expanded lumen against recoil and remodeling. Stents, which are typically made of a biocompatible metal, become incorporated within the vascular wall upon re-growth of the endothelium and are not removable. This feature can compromise re-treatment or treatment of distal portions of the stented vessel. Metallic stents can initiate a thrombogenic and immunogenic response, such as a foreign body response with inflammation. Moreover, metal stents have limited flexibility, making them difficult to deploy in smaller vessels. Because metal stents are permanent, their continued presence may interfere with future interventions and may lead to corrosion, perforation, and potential aneurysm. On an individual basis, the various metals being used may cause an allergic reaction.

Second generation stents have been developed in an attempt to address the problems listed above. Temporary metallic stents address the issue of permanence, but excessive trauma is associated with the retrieval process. Stent coatings, such as genetically engineered endothelial cells or various polymers have been employed in an attempt to reduce thrombogenicity. Polymers such as nylon, silicone, polyurethane, and fibrin have been tested with mixed results. Though data suggest some reduction in thrombus formation, other problems, including donor infection, optimization of formulation and delivery, and immunological response remain to be addressed. Stents comprised entirely of polmeric material offer an alternative to metallic stents. However, deployment techniques requiring heat, such as that required for polycaprolactone, can cause denaturation of adjacent tissues, and acidic breakdown products of biodegradable polymers can cause a significant inflammatory response. An additional consideration with biodegradable stents is the potential for atrophy of the musculoelastic elements in the arterial wall while the stent is in place, which may lead to aneurismal dilatation after the stent has been degraded. Finally, the polymer stents are intrinsically weaker than their metallic counterparts and additional bulk may be required to achieve adequate hoop strength.

Drugs capable of inhibiting thrombus formation and/or neointimal proliferation can be utilized, but systemic delivery of several appropriate and promising pharmaceutical agents has failed to demonstate clinical significance in reducing restenosis. This could result from a failure to achieve adequate local doses because of the toxic effect of high systemic delivery. Local delivery results in high local concentrations (up to ten times systemic concentrations) while avoiding toxicity. Polymeric stents or stent coatings can be used to incorporate or bind drugs with ensuing controlled, sustained, local drug delivery at the site of vascular injury.

Pharmaceutical coated stents are presently in the market and are being increasingly used. By attaching antithrombotic or antiproliferative pharmaceutical agents to the stent surface, reductions in restenosis rates have been reported. However, the mode of drug attachment can alter the biological activity of the compound, possibly due to masking of active sites or undesirable conformational changes. Furthermore, stents generally cover less than 10% of targeted vessel wall segments, resulting in nonuniform delivery to the arterial wall. Recent reports suggest an unfavorably high rate of allergic reactions and occlusive thrombotic responses to the coated stents.

What is needed, therefore, is a method for stabilizing the dilated vascular wall without the introduction of a foreign body, and also for maintaining the diameter of an artery expanded through balloon dilation in order to restore and maintain blood flow. What is also needed is a method for providing targeted, local drug delivery to the site of arterial expansion. Ideally, such a method should minimize the risks of restenosis and immune response. Such a method would also be useful for the local delivery of drugs, skin care materials, sunscreens, and cosmetics to the skin and to other anatomical, physical, surgical, and medical sites.

SUMMARY

This invention is directed to naphthalimide compounds and their use in tissue bonding and protein cross-linking. This invention also pertains to devices and methods for tissue and arterial repair, preservation of expanded internal luminal diameters, and local delivery of drugs, skin care materials, sunscreens, and cosmetics. In particular, the present invention utilizes naphthalimide compounds, which produce an adhesive agent when applied to the surface of a biomaterial and activated by an activating agent. The present invention also particularly relates to naphthalimide labeled biomolecules that may be used to link tissue surfaces together without direct activation of the contacted tissue area with an activating agent, such as light energy.

One aspect of this invention particularly pertains to naphthalimide compounds. Upon activation by an activating agent in an environment independent of the presence or absence of oxygen, naphthalimide compounds generate activated species. The activated species can cause structural changes in lipid and any associated proteins and polypeptides, extra- or intra-cellular or transmembrane, leading to polymerization and cross-linking.

Embodiments of the present invention include naphthalimide-substituted biomolecules. The naphthalimide compound may be a 4-amino-1,8-naphthalimide or a modified naphthalimide, such as Bradsyl. The biomolecule may be chitosan or another macromolecular species. The naphthalimide-substituted biomolecule may be in gel form and within a compatible pH range. When irradiated with light in the 400-500 nm absorption range, the species forms a chemically-reactive species that, upon contact, bonds connective tissues together and bonds collagenous biomaterial together and to other connective tissues. The biomolecular chitosan moiety of the photochemical may favorably provide an environment which stabilizes and protects the reactive species, derived by the photochemical reaction, until contacted with a connective tissue substrate. Thus, the naphthalimide-labeled biomolecule is capable of bonding tissues with or without subsequent irradiation of the contacted tissue area.

One embodiment of the present invention, in which the chemically-reactive tissue bonding species is formed in the absence of the tissue substrate and is sufficiently long-lasting, obviates the need for direct illumination of the photochemical covered tissue surfaces during bonding. The naphthalimide-labeled biomolecule acts as an adhesive which allows controlled delivery of the tissue-bonding compound and facilitates bonding in the absence of excessive compression. This is essential in vascular applications, in which it is imperative to avoid intraluminal bonding which could result in obstructed blood flow. The present invention also provides immediate hemostasis and promotes primary healing in the absence of excessive proliferation or inflammation. The use of the naphthalimide-labeled biomolecules of the present invention also has the potential to reduce operative times.

Naphthalimide compounds of the present invention are useful for various tissue bonding applications, including vascular patch repair applications, and for constructing three dimensional objects from biomaterials, such as prostheses or grafts. Furthermore, the naphthalimide compounds of the present invention may be sterilized by standard steam autoclaving for safe biological use without losing the ability to bind tissue.

Another embodiment of the present invention relates to methods for stabilizing the expanded shape of a dilated vessel wall post-angioplasty. Delivery of a naphthalimide compound to an expanded arterial region, followed by activation by an activating agent, can initiate cross-linking of proteins within the arterial wall and cause the post-angioplasty configuration of the lumen to be maintained. Use of the naphthalimide compounds within the expanded artery preferably creates a relatively smooth vessel lumen, limiting activation of the coagulatory process and thrombus formation which might otherwise result from healing of the intimal and medial arterial dissections. The proximity of the tissue bond is determined by the length of the structural bridge, or spacer moiety, between the two reactive naphthalimide rings. Such close apposition limits exposure of subendothelial elements to circulating blood and vasoactive factors associated with the restenosis process. Replacement of the presently used metallic or polymer stents with this endogenous, non-metallic "stent" would favorably eliminate the post-operative problems associated with these implanted devices and would reduce device costs.

A further embodiment of the present invention relates to methods for delivering a pharmaceutical agent to a targeted site on a tissue surface, such as an arterial wall. A pharmaceutical agent, such as an anti-restenotic agent, can be photochemically anchored to the arterial wall through a covalent linkage between the pharmaceutical agent the naphthalimide compound at an inert site, thus preserving the biological activity of the agent. The naphthalimide compound is then photochemically activated by an activating agent and linked to collagen and other proteins in the arterial wall. Linkage of the pharmacological agent to the tissue site limits reperfusion washout. Cleavage of the tether will release the pharmacological agent for potential cellular interaction, if this is desired. This photochemical tethering of a pharmacological agent to targeted tissue areas may be used in association with various applications to provide local delivery of drugs, skin care products, sunscreens, and cosmetics to the skin and to many other anatomical, physical, surgical, or medical sites.

DETAILED DESCRIPTION OF PREFERRED EMBODIMENTS

Figure 1:
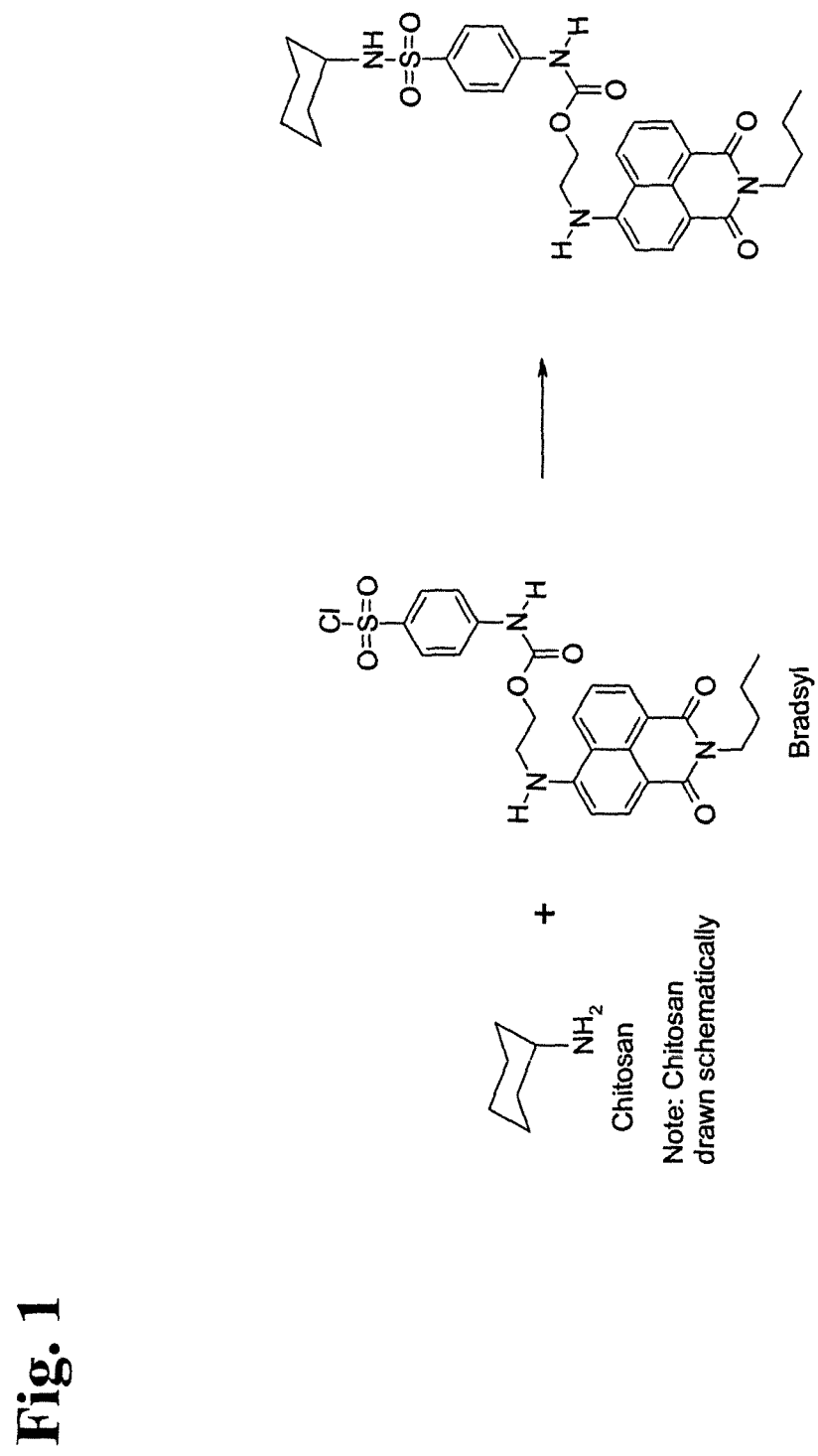
FIG. 1 is a generalized representation of the labeling of chitosan with a naphthalimide compound (Bradsyl).

One aspect of the current invention pertains to naphthalimide compounds and their use in tissue bonding and protein cross-linking applications. The naphthalimide compounds can be activated in the simultaneous presence of an activating agent and a target tissue or protein, causing the naphthalimide compounds to become an adhesive agent and initiate protein cross-linking. The naphthalimide compounds may be linked to biomolecules, such as chitosan, creating naphthalimide-labeled compounds. These naphthalimide-labeled compounds may also be activated by an activating agent prior to contact with tissue and carry out subsequent tissue bonding under "dark" conditions, or in the absence of direct tissue illumination.

The naphthalimide compounds are useful for tissue bonding, and in particular, for applications such as arterial repair and stabilization of an expanded arterial wall. In addition, the naphthalimide compounds can be linked with pharmaceutical agents, providing targeted delivery of the pharmaceutical agents to tissue surfaces.

As used herein, the word "dye" is interchangeable with the word "compound," as referred to non-azo 1,8-naphthalimides. See U.S. Pat. Nos. 5,235,045; 5,565,551; 5,766,600; 5,917,045; and 6,410,505; the content of each of these patents is incorporated by reference herein.

A "non-azo compound" or dye is one that does not possess a functional grouping having two nitrogen atoms connected by a double bond.

A "nucleofuge" is any group which can be displaced from a molecule by a nucleophile. Examples of nucleofuges include halogens, sulfonate esters, and quaternary ammonium salts.

As used herein, the words "unsatisfied valences" mean less than tervalent. Thus, any nitrogen atom which is less than tervalent or tri-coordinate contains unsatisfied valences.

The "activating agent" as used herein denotes a means or an agent that is capable of activating, exciting, or sensitizing a photoactive compound. The activating agent can be radiated energy, electromagnetic energy, laser, electric current, electrons, thermal neutrons or chemicals. The electromagnetic spectrum can include visible light, xenon light, laser light, near infrared and ultraviolet light. The laser or other radiation energy can be continuous or pulsed. The pulsed energy used is such that the energy supplied has a multiple number of short pulses of relatively high energy, but at the same time, has a much lower average energy rate. The laser could be a Helium-Cadmium laser, argon ion laser, a solid state laser, a gas discharge laser, krypton laser, argon ion pumped dye laser, or hollow cathode metal vapor laser or semiconductor diode laser, and others. Even sources such as conventional filament lamp source with appropriate filtering, an arc lamp source with appropriate filtering, even a pulsed xenon flash lamp with appropriate filtering could be used, or light emitting semiconductor such as GaN and ZnSe diodes.

The term "body tissue" as used herein is to be understood to include "body fluid," red blood cells, white blood cells, platelets, cryo precipitate from blood plasma, other plasma proteins, bone marrow, skin, blood vessel wall, nerve sheath, meniscal cartilage, fermoral articular cartilage, cornea, ligament, tendon and other tissues from an animal or a human.

The term "animal" as used herein is to denote any animal; this includes human and other domestic and farm animals.

The term "carrier" as used herein denotes a vehicle, a solution containing water, buffers, serum, serum proteins, lipoproteins, artificial bio-membranes, micelles, liposomes, monoclonal antibodies, carbohydrates, cyclodextrans, organic solvents or other pharmaceutically acceptable, or compatible, solutions. The carrier, or vehicle, used is pharmaceutically compatible in that it is relatively non-toxic to the normal cells and normal tissues and it does not react with the solute or therapeutic agent contained therein.

The phrase "effective amount" as used herein is to denote the concentration or level of the compound that can attain a particular end, such as cross-linking, without producing pronounced toxic symptoms.

The term "derivative" as used herein is to denote a compound that is derived from some other base compound and usually maintains the general structure of the base compound.

In general, the covalent reactions initiated by the activated form of these dyes can result in chemical alteration of amino acid residues, of protein and peptide conformation and function, and can cross-link the amino acid residues, peptides, and proteins. Thus, this class of dyes can be used to link desired molecular and biomolecular species to peptides, proteins, cells, and biological tissues as well as other physiological substrates containing nucleophilic or other reactive groups, and to cross-link peptides, proteins, tissues, and other substrates containing nucleophilic or other reactive groups selectively upon application of an activating agent, such as electromagnetic radiation with wavelength corresponding in absorption spectrum of the dye absorption spectrum. In addition, graft or prosthetic materials containing nucleophilic or other reactive groups can be linked to the activated naphthalimide. See, U.S. Pat. No. 5,235,045.

The appropriate electromagnetic radiation absorption spectrum includes the ultraviolet through visible light to near infrared and the K-alpha, etc., X-ray absorption energies of the molecular halogen substituent. Other activating agents include thermal neutrons which could be used to activate boron-containing 1,8-naphthalimide dyes.

The partitioning of non-azo 1,8-naphthalimide dyes into hydrophobic or hydrophilic regions of a tissue, and the capability of activating covalent chemical reactions with nucleophilic amino acid residues allows cross-linking of peptides or proteins located either extra- or intra-cellularly or associated with the bilayer membrane selectively upon activation. No photochemical cross-linking occurs until the dye has been activated by an activating agent, such as light.

One embodiment of the present invention is a species of compound in which a naphthalimide compound is coupled to a biomolecular moiety. The naphthalimide is attached covalently via the 4-amino moiety through a photochemically inert carbon species chain at the deacylated amino species positions on the chitosan monomers. The photochemical reaction of the naphthalimide species yields a tissue chemical species which reacts covalently with biological connective tissue chemical species. Without wanting to be bound by theory, the biomolecular moiety provides an environment which stabilizes and protects the reactive species until contacted with a connective tissue substrate. Preferably, the naphthalimide compound is 4-amino-1,8-naphthalimide and the biomolecular moiety is chitosan.

The naphthalimide-labeled biomolecule may be represented as:

D-B wherein D is the naphthalimide compound or molecule or dye and B is the biomolecule.

Any suitable biomolecule B can be labeled by the naphthalimide compounds in accordance with the present invention. In particular, biomolecules which may be labeled by the naphthalimide molecule or compound include, but are not limited to, chitosan, protein, hydrolyzed protein, and carbohydrates. Preferably, the labeled biomolecule is chitosan. The macromolecular chitosan should be present in partially deacylated form. Chitosan is derived from the deacetylation of chitin. The macromolecular chitosan used should be at least 70% deacetylated, more preferably 85% or more deacetylated.

Figure 2:
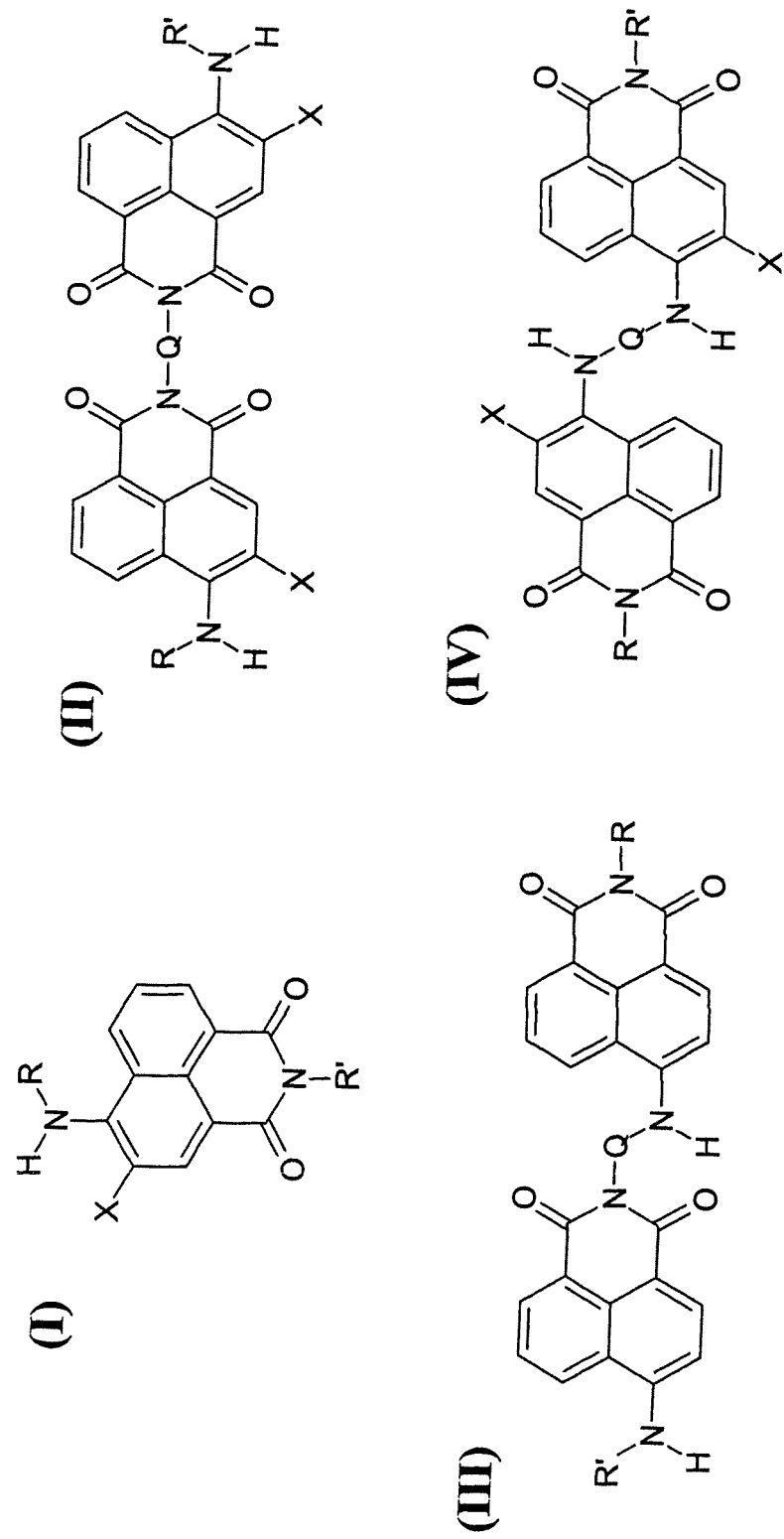
FIG. 2 shows four representative structures (I)-(IV) of non-azo 4-amino-1,8-naphthalimide compounds.

In a preferred embodiment, the naphthalimide compound or molecule D is a 4-amino-1,8-naphthalimide compound represented as any of the four structures (I)-(IV) shown in FIG. 2, wherein R, R', and Q are straight-chain or branched chain alkyl groups having from 2 to 200 carbons, optionally having one or more ether, amide, or amine groups, and X is hydrogen, a halogen, a sulfonate ester, or a quaternary ammonium salt. The structures (I)-(IV) may represent hydrophilic or lipophilic naphthalimide compounds. When substituent X is hydrogen, the compound is hydrophilic. When substituent X is a nucleofuge, such as a halogen, a sulfonate ester, or a quaternary ammonium salt, the compound is hydrophobic or lipophilic. The biomolecule B is preferably linked to the naphthalimide compound at one of the 4-amino groups, or at an end of one of the R or R' groups.

In another preferred embodiment, the naphthalimide compound D has the structure:

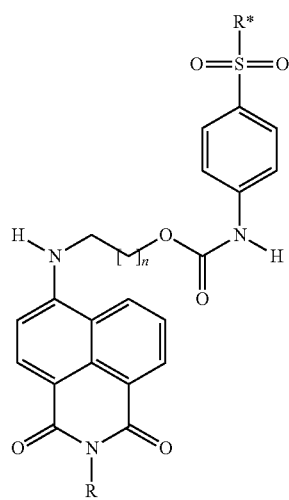

which is a mixture of stereoisomers, wherein:
n is an integer between 1 and 20;
R is selected from the group consisting of $CH_3$, $C_4H_9$, $C_6H_{13}$, $(CH_2)_2N(CH_3)_3+$, $CH_2COOH$, $(CH_2)CH_2(CH_3)_2COOH$, and $(CH_2)CH_2(CH_3)_2COOCH_3$; and
R* is a bond between D and B.

A preferred embodiment is also directed to a biomolecule that has been labeled with a modified naphthalimide called Bradsyl. Bradsyl chloride, a dark reactive naphthalimide, is a fluorescent tag structurally similar to Dansyl chloride and having an IUPAC name of (4-Chlorosulfonyl-phenyl)-carbamic acid 2-(2-butyl-1,3-dioxo-2,3-dihydro-1H-benzo[de]isoquinolin-6-ylamino)-ethyl ester. Labeling chitosan with Bradsyl results in Bradsyl chitosan, a molecule with improved bonding characteristics. FIG. 1 shows the structure of Bradsyl, as well as a generalized representation of labeling chitosan with Bradsyl. A rigid hydrophobic spacer (an aromatic ring) places the naphthalimide away from the chitosan backbone, while the hydrophobic terminal butyl group tends to further pull the naphthalimide into hydrophobic environments. Without wanting to be bound by theory, this tendency likely maximizes naphthalimide interaction with hydrophobic tissue environments and productive photochemical reaction sites within the tissue, promoting bonding at the tissue-filler interface and yielding high bond strengths with a minimal amount of compression.

Bradsyl and Bradsyl derivatives may be used to label different biomolecules. One skilled in the field can vary the structural components of the Bradsyl molecule to tailor the properties to the desired results. The spacer between the naphthalimide and the dark reactive group of Bradsyl can be varied in length and in character. Longer and shorter alkanes can be attached to the bottom of the naphthalimide. The neutral hydrophobic end can be changed to a group with a positive or negative charge, or to a hydrophilic end with or without a positive or negative charge. Finally, other derivatives can utilize amino acids or derivatives of amino acids. The labeled biomolecule can be varied as well. In preferred embodiments, Bradsyl chitosan was synthesized by using Bradsyl to label chitosans. The Bradsyl chitosan compound may be referred to alternately as Bradsyl-modified chitosan, Bradsyl-labeled chitosan, or Bradsyl-labeled acid soluble chitosan.

A preferred embodiment of the present invention is directed to the bonding of natural biomaterials containing protein, such as connective tissue, as well as synthetic materials. Naphthalimide-labeled biomolecules of the present invention are capable of bonding these proteinaceous substrates with or without subsequent irradiation of the tissue sections contacted with the adhesive gel. The naphthalimide-labeled compounds may be "activated" prior to contact with the substrate through irradiation or ambient light. Preferably, the naphthalimide-labeled compounds are first irradiated with blue light in the wavelength range of about 400 nm to about 500 nm. The "activated" naphthalimide-labeled compounds are then applied to the substrate sections to be bonded. Preferably, minimal compression of at least about 0.025 $kg/cm^2$ is applied to the substrate sections for at least about one minute and more preferably for at least about five minutes. Additional irradiation is not necessary, eliminating the need for direct illumination of the bonded substrates.

Numerous permutations in the activation protocol (i.e., biomolecule and naphthalimide compound concentrations, pressure, light intensities, and exposure times) may be used to further enhance overall bond strengths and improve reproducibility.

In preferred embodiments, the naphthalimide-labeled compounds may be used to bond a body tissue to a proteinaceous substrate, such as an endogenous body tissue, an exogenous biological material, or an exogenous synthetic material. An additional preferred embodiment of the present invention is directed to the use of a naphthalimide-labeled compound in applying a patch for vascular repair. In particular, the naphthalimide-labeled compound can be used to bond a natural or synthetic patch substrate to a body tissue, such as the adventitia of an artery, to repair a tissue or arterial defect, using the same procedure for bonding tissue segments.

A further preferred embodiment of the present invention is directed to the construction of three dimensional objects from biomaterials by utilizing a naphthalimide-labeled compound to bond portions of the biomaterials or cross-link proteins and shape them accordingly. In particular, the naphthalimide-labeled compound may be used to shape tubular vascular grafts from flat pieces of tissue or to cross-link the elements of a tissue homogenate in suspension to form a three-dimensional object of desired conformation.

Additional preferred embodiments relate to the use of 4-amino-1,8-naphthalimide compounds in the creation of an endogenous "stent," or the stabilization of an expanded arterial wall after angioplasty, and local drug delivery through the tethering of pharmacological agents to tissue surfaces via the naphthalimide compounds. Naphthalimide compounds which may be used in accordance with these preferred embodiments include those described in U.S. Pat. Nos. 5,235,045, 5,565,551, 5,766,600, 5,917,045, and 6,410,505, and U.S. patent application Ser. No. 10/176,824, the content of each of which is incorporated by reference herein. These naphthalimide compounds are particularly useful for applications involving stabilizing expanded arterial diameters and local drug delivery.

Preferably, the naphthalimide compound should be a non-azo 4-amino-1,8-naphthalimide. The naphthalimide compound can be monomeric, dimeric, hydrophilic, or lipophilic. The naphthalimide compound may have one of the structures (I)-(IV) shown in FIG. 2, wherein R, R', and Q are straight-chain or branched chain alkyl groups having from 2 to 200 carbons and optionally having one or more ether, amide, or amine groups. The structures (I)-(IV) may represent hydrophilic or lipophilic naphthalimide compounds. When substituent X is hydrogen, the compound is hydrophilic. When substituent X is a nucleofuge, such as a halogen, a sulfonate ester, or a quaternary ammonium salt, the compound is hydrophobic or lipophilic.

A preferred embodiment of the present invention is directed to the use of naphthalimide compounds in stabilizing the diameter of an expanded arterial wall. The naphthalimide compound should be infused into the arterial wall after balloon inflation has deformed the wall and enlarged the vessel lumen. Light irradiation through the transparent balloon wall, such as by a fiber optic delivered within the balloon, then effects the formation of an endogenous "stent" by cross-linking endogenous plaque and wall proteins. With protein cross-linking occurring in the dilated state, the post-angioplasty configuration of the lumen is maintained. The proximity of the tissue bond will be determined by the length of the structural bridge between the two reactive naphthalimide rings. Molecular lengths of 6 to 50 angstroms have been prepared as simple naphthalimide molecules. Longer molecules may be synthesized by attaching the naphthalimide groups to appropriate macromolecules.

There are many benefits of using the naphthalimide compounds in accordance with the present invention to produce an endogenous "stent," compared to traditional angioplasty. After angioplasty, the artery is stretched and the endogenous plaque is fractured and released at the shoulders, exposing the subendothelium to circulating vasoactive factors and cytokines. However, with traditional angioplasty, the artery undergoes restenosis with elastic recoil to its original dimensions, with neointimal formation in response to injury that further reduces the luminal area. By maintaining the post-angioplasty configuration while tacking down intimal flaps, there is less elastic recoil, maintained compression of media and plaque, and limited neointimal formation, resulting in increased luminal area.

A further preferred embodiment of the present invention is directed to the use of naphthalimide compounds for local delivery of any suitable pharmacological agent to tissue or artery regions. In particular, a preferred embodiment encompasses local delivery of pharmacological agents to the arterial wall luminal surface following coronary balloon angioplasty, to reduce restenosis. The naphthalimide compounds may be used to not only cross-link intramedia proteins and stabilize the dilated arterial wall, but also to link anti-restenotic agents to targeted components of the arterial wall immediately following balloon angioplasty. Anti-restenotic drugs such as heparin, taxol, sirolimus, and other suitable pharmacological agents, may be tethered to the arterial wall via the naphthalimide compounds. The naphthalimide compounds may also be used to tether pharmacological agents to tissues at other anatomical, physical, surgical, and medical sites to treat various conditions.

A preferred device for achieving local tethering of the anti-restenotic drugs to the arterial wall ideally includes a multi-functional vascular catheter with balloon dilation capability, the capability to deliver the anti-restenotic agent in aqueous medium to sites along the contact interface between the expanded balloon and luminal surfaces, an optical fiber with its tip located in the balloon axis which can emit light uniformly over the balloon-contacted arterial surface for photochemical activation, and a perfusion channel to maintain blood flow through the device to regions beyond the balloon site.

Figure 3:
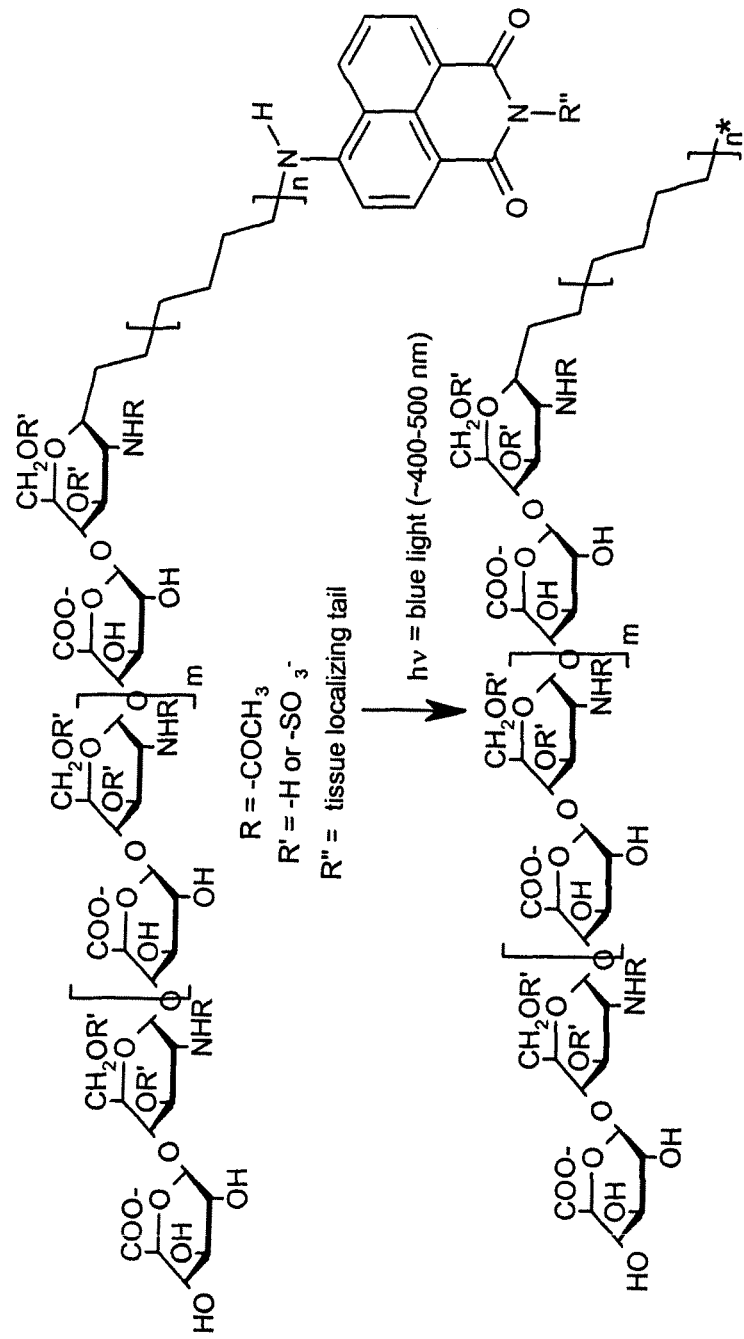
FIG. 3 is a representation of the process for tethering heparin to a tissue substrate using a naphthalimide compound.

As shown in FIG. 3, an anti-restenotic drug, such as heparin (with m repeating units), is covalently attached to the naphthalimide compound by a tether (length n). Subsequent light activation results in the creation of a reactive site (*) that quickly bonds with adjacent tissue substrates. This provides a means by which to anchor the heparin molecule within the arterial wall. This will minimize the loss of heparin, or other potential pharmaceutical agents, to reperfusion washout, resulting in enhanced local drug delivery. By subsequent natural, endogenous cleavage of the tether, the pharmacological agent can be released for potential cellular interaction, if this is desired. Through the nature and identity of chemical species comprising the tether linkages (e.g., polypeptide, polyester, etc.), the rate of cleavage of the tether by simple hydrolysis and other enzymatic cleavage can be modulated, thus controlling the rate and duration of drug delivery. Retention in linked form may be desirable for some pharmacological agents.

A further preferred embodiment of the present invention is directed to the use of naphthalimide compounds for local delivery and tethering of drugs, skin care materials, sunscreens, and cosmetics to the skin. To accomplish this, a biomolecule which has been labeled with a naphthalimide compound is also modified with an additional compound having the desired functional property. After physical contact with the skin, the modified biomolecule and its attached functional compound are tethered to the tissue surface. In this way, compounds such as sunscreen can be locally delivered and tethered to the skin to increase their residence time, their resistance to water, perspiration, and rubbing, their coverage, and their effectiveness.

The product can be represented as:

D-B-F wherein D is a naphthalimide molecule, B is a biomolecule, and F is a functional molecule of a pharmacological agent, a skin care material, a sunscreen, such as a UV blocker, or a cosmetic.

In particular, there are three preferred examples of types of sunscreen compounds which can be linked to naphthalimide-labeled biomolecules and tethered to the skin: compounds containing sulfonic acid functional groups, compounds containing alcohol functional groups, and compounds containing amine functional groups.

Figure 4:
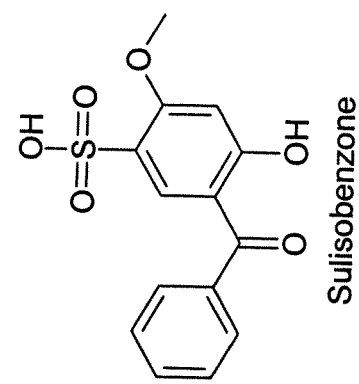
FIG. 4 shows two example sunscreen compounds having sulfonic acid functional groups.
Figure 4:
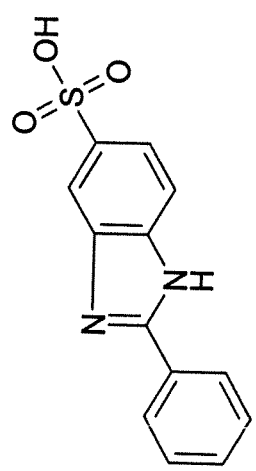
Figure 5:
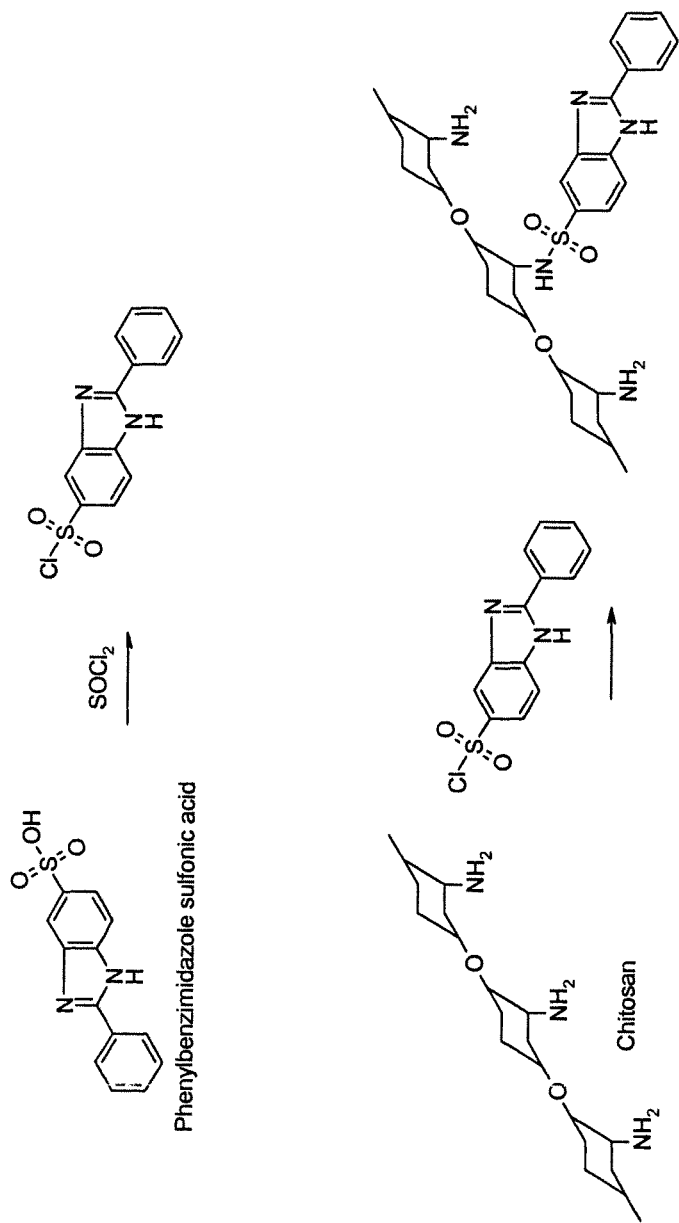
FIG. 5 shows an example of a process used to attach a sunscreen compound having a sulfonic acid functional group to chitosan.
Figure 6:
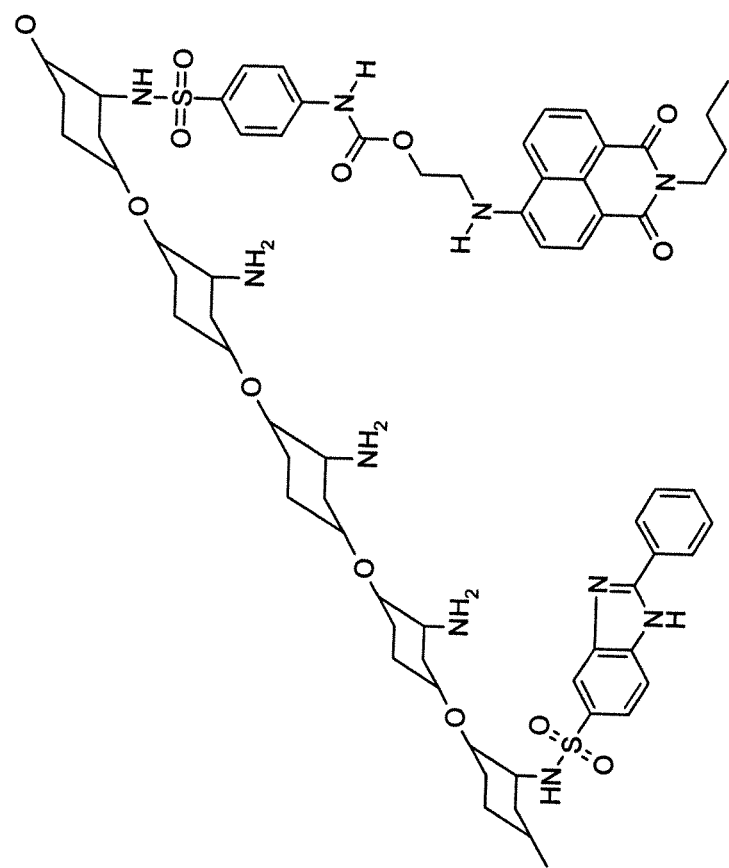
FIG. 6 shows an example of a chitosan backbone having a sunscreen compound and a naphthalimide compound covalently attached.

Preferred examples of sunscreen compounds containing sulfonic acid functional groups include phenylbenzimidazole sulfonic acid and sulisobenzone, which are illustrated in FIG. 4. The sulfonic acid functional group is used to link these compounds to a biomolecule such as chitosan. In one specific example, as shown in FIG. 5, phenylbenzimidazole sulfonic acid is converted to the sulfonyl chloride derivative, which is directly linked with the primary amine group of chitosan to give the linked sunscreen compound. The naphthalimide molecule or compound, although not shown in FIG. 5, is also linked to the biomolecule. FIG. 6 shows a representative example of the covalent attachment of both a sunscreen agent and a naphthalimide to a schematic representation of a chitosan backbone. The sunscreen agent, or other functional compound, and the naphthalimide molecule may be attached in either order or simultaneously. Approximately one naphthalimide compound per one hundred sugar monomer units is preferred, but that ratio may be higher or lower. Approximately one sunscreen agent per ten sugar monomer units is preferred for effective sunscreen protection, but that ratio may be higher or lower to provide the effective sunscreen protection profile desired.

Figure 7:
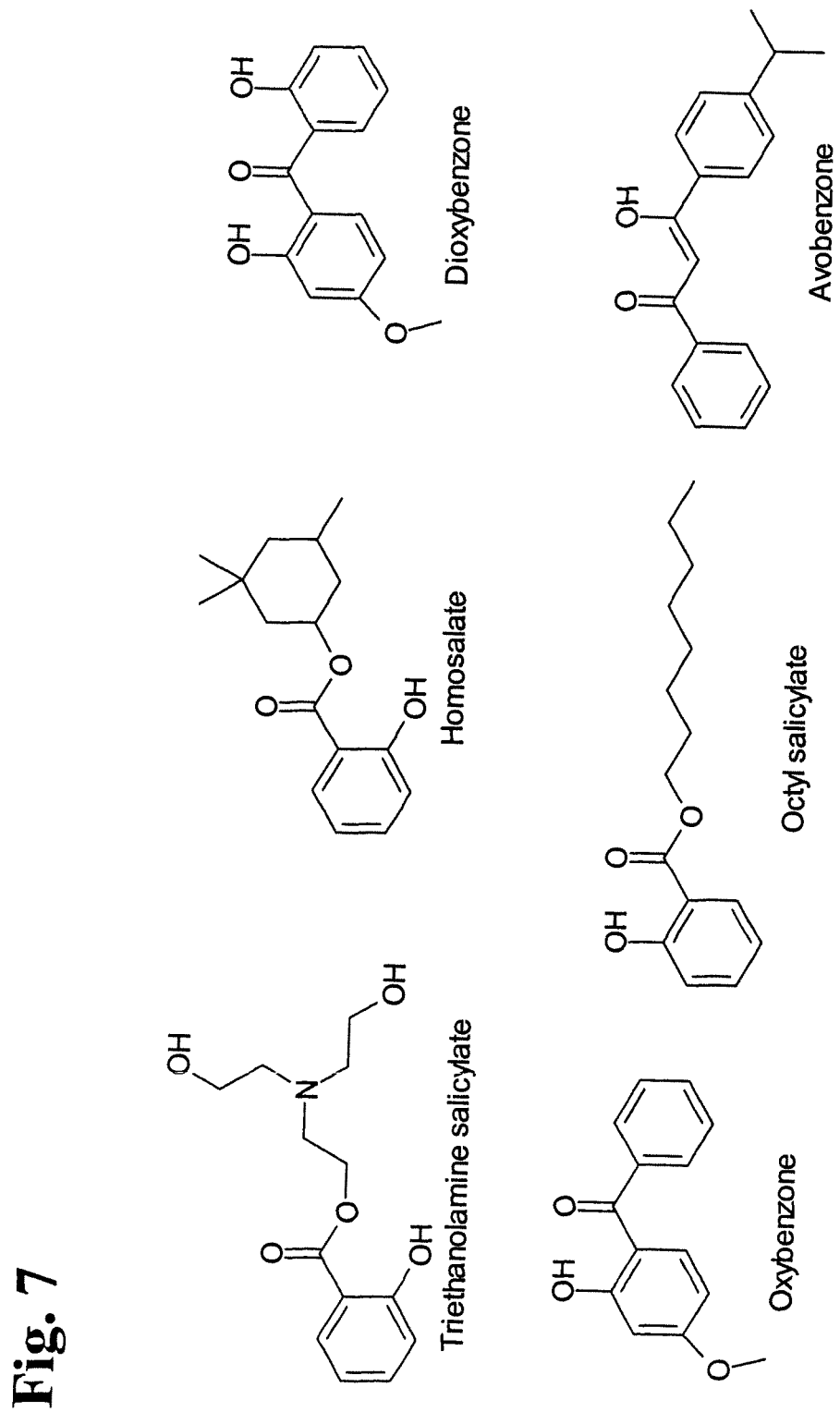
FIG. 7 shows six example sunscreen compounds having alcohol functional groups.
Figure 8:
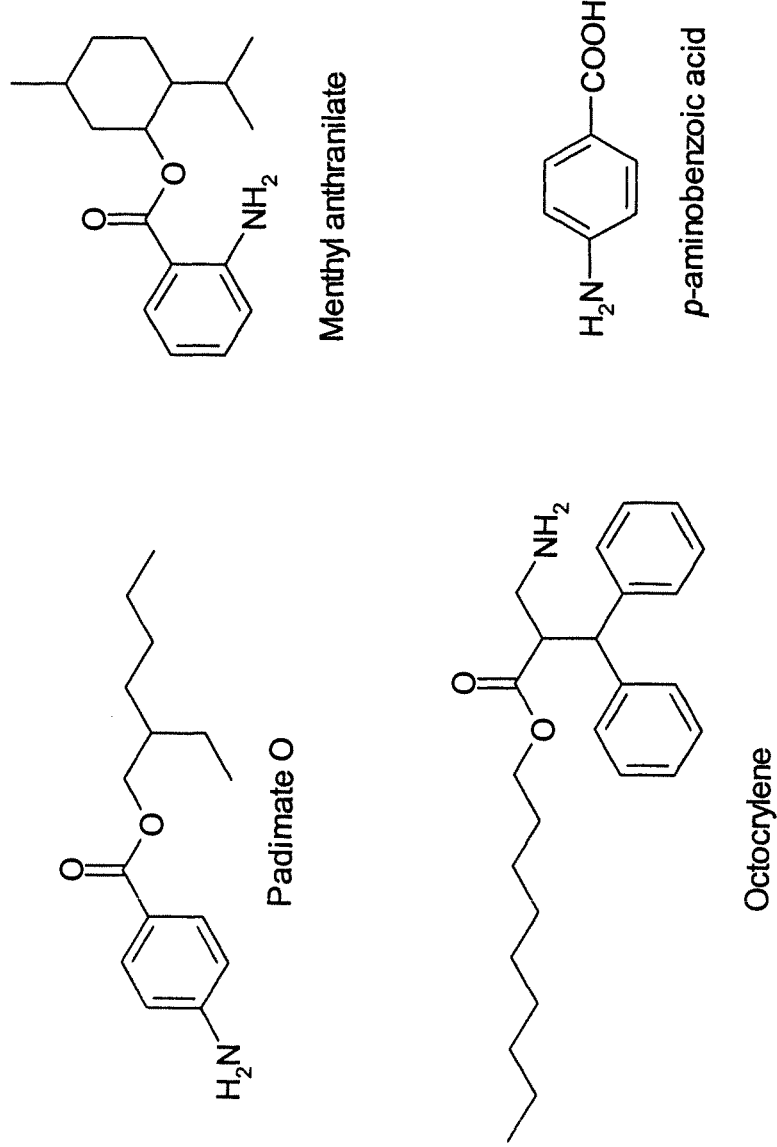
FIG. 8 shows four example sunscreen compounds having amine functional groups.
Figure 9:
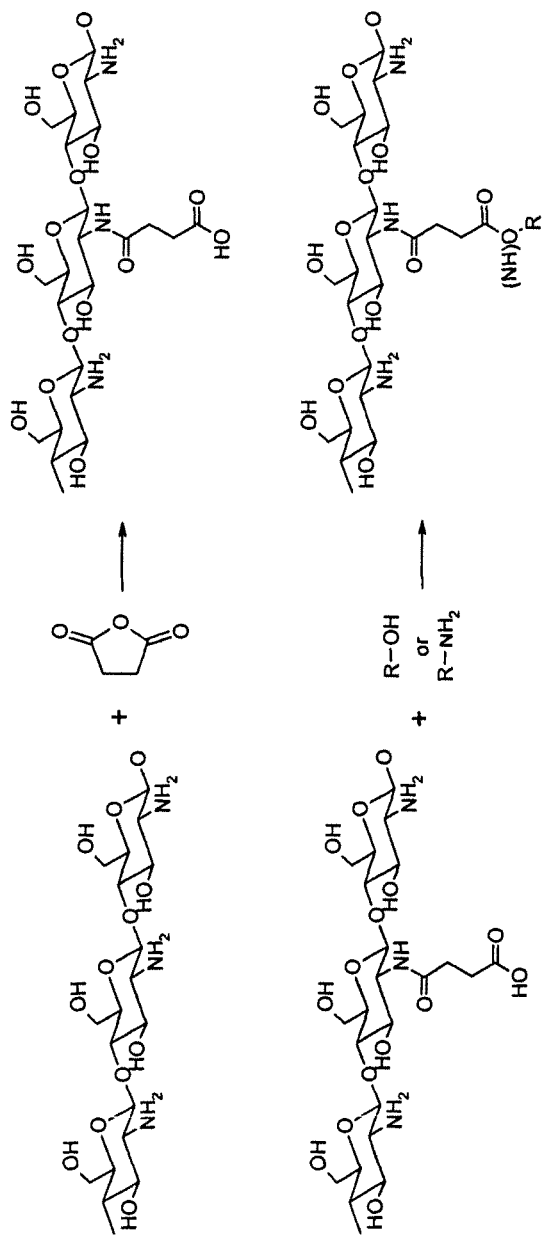
FIG. 9 shows an example of a process used to attach a sunscreen compound having an alcohol or an amine functional group to chitosan.

Preferred examples of sunscreen compounds containing alcohol functional groups include triethanolamine salicylate, homosalate, dioxybenzone, oxybenzone, octyl salicylate, and avobenzone, as illustrated in FIG. 7. Preferred examples of sunscreen compounds containing amine functional groups include padimate 0, menthyl anthranilate, octocrylene, and p-aminobenzoic acid, as illustrated in FIG. 8. Compounds in both of these groups can be attached to succinyl chitosan by the formation of either an ester or an amide functional group. In a specific example, as shown in FIG. 9, chitosan is modified by succinic anhydride to form succinyl chitosan. The carboxylate formed would be converted into an ester or amide using an activating agent such as EDC. The naphthalimide compound, although not shown in FIG. 9, is also linked to the biomolecule.

Example 1

Synthesis of Bradsyl

The first step involves the synthesis of 4-(2'-aminoethyl)amino-N-butyl-1,8-naphthalimide. To a solution of 4-bromo-1,8-naphthalic anhydride (2.30 g, 9.9 mmol) in ethanol (100 mL) was added 1-butylamine (0.73 g, 10.0 mmol). The mixture was stirred at 68° C. for 24 hours. The general reaction scheme is shown below.

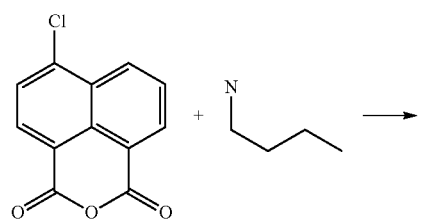

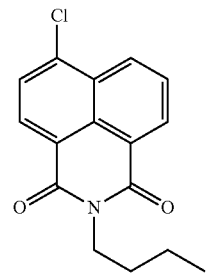

Next, 2-aminoethanol (6.0 g, 100 mmol) was added. Heating was continued for a further 48 hours, after which the solvent was removed by evaporation under reduced pressure. Recrystallization of the resultant yellow solid from toluene afforded 4-(2'-aminoethyl)amino-N-butyl-1,8-naphthalimide (1.75 g, 56%) as yellow crystals, with a melting point of about 128-132° C. The general reaction scheme is shown below.

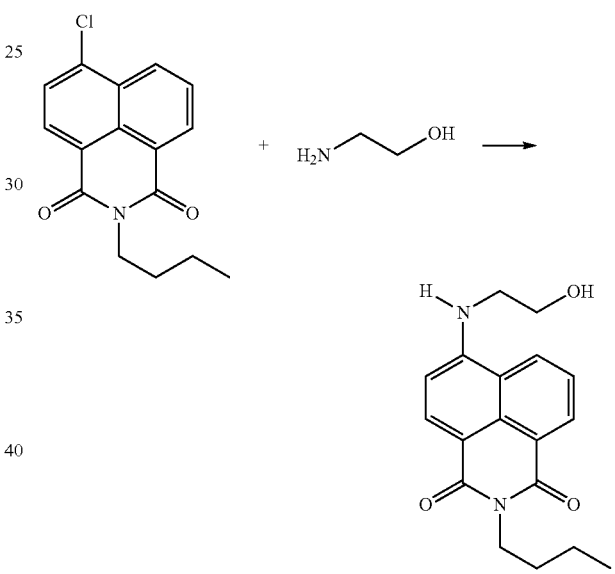

Experimental data for 4-(2'-aminoethyl)amino-N-butyl-1,8-naphthalimide: $v_{max}$ (cm$^{-1}$): 3350-2800 (br., N—H str.). 1685 (C=O), 1640 (C=O), 1587, 1359, 782. $^1$H NMR (CDCl$_3$): δ 8.59 (d, J=7.4 Hz, 1H, C7-H), 8.47 (d, J=8.4 Hz, 1H, C2-H), 8.19 (d, J=8.4 Hz, 1H, C5-H), 7.63 (d, J=8.4 Hz, of d, J=7.4 Hz, 1H, C6-H), 6.72 (d, J=8.4 Hz, 1H, C3-H), 6.17 (br. t, 1H, NH). 4.17 (d, J=7.3 Hz, of d, J=7.7 Hz, 2H, CH$_2$—N), 3.43 (d, J=6.1 Hz, of t, J=5.3 Hz, 2H, NH—CH$_2$), 3.19 (d, J=6.2 Hz, of d, J=5.1 Hz, 2H, CH$_2$—NH$_2$), 1.35-1.8 (m, 6H, CH$_2$CH$_2$CH$_3$, NH$_2$), 0.97 (t, J=7.3 Hz, 3H, CH$_3$). m/z: 313 (M+H+1, 23), 312 (M+H; 100), 295 (31), 281 (25), 268 (51), 238 (24), 224 (63).

The next step generated Bradsyl, or 4-(2-[{4-chlorosulfonylphenyl}-aminocarbonyloxy]ethyl)amino-N-butyl-1,8-naphthalimide. To a solution of 4-(2'-hydroxyethyl)amino-N-butyl-1,8-naphthalimide (1.70 g, 5.4 mmol), prepared above, in anhydrous THF (50 mL), p-chlorosulfonylphenyl isocyanate (2.18 g, 10 mmol) was added. The resultant mixture was stirred under a nitrogen atmosphere for 24 hours, and the mixture was then vacuum filtered to afford the urethane as a yellow solid. The general reaction scheme is shown below.

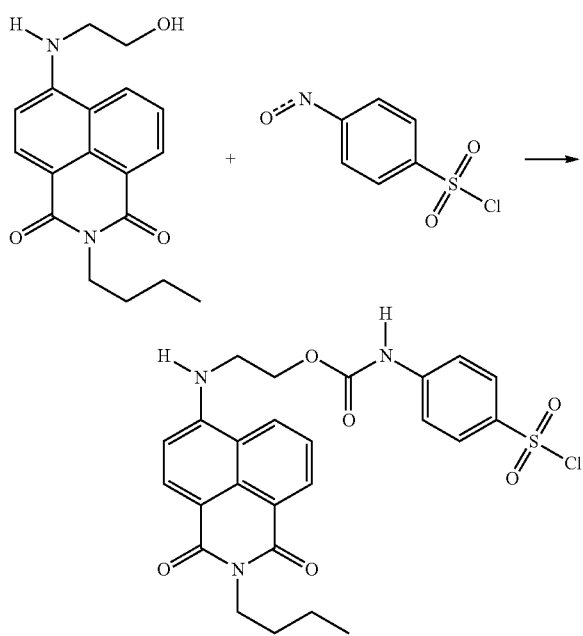

Experimental data for 4-(2-[{4-chlorosulfonylphenyl}-aminocarbonyloxy]ethyl)amino-N-butyl-1,8-naphthalimide: $v_{max}$ (cm$^{-1}$): 3426, 3299 (N—H str.), 3195, 3121, 3058, 2970, 2868 (C—H str.), 1741, 1703 (imide C=0 str.), 1636 (urethane C=O str.), 1593, 1551, 1470, 1357, 1174, 777. $^1$H NMR (DMSO-d$_6$): δ 9.85 (br. s, 1H, NHCO$_2$), 8.73 (d, J=8.4 Hz, 1H, C7-H), 8.44 (d, J=7.0 Hz, 1H, C5-H), 8.29 (d, J=8.4 Hz, 1H, C2-H), 7.3-7.8 (complex m, 5H, ClSO$_2$C$_6$H$_4$, C6-H), 6.89 (d, J=8.5 Hz, 1H, C3-H), 4.41 (br. t, J=4.6 Hz, of d, J=7.3 Hz, 2H, O—CH$_2$), 4.01 (t, J=6.7 Hz, 2H, N—CH$_2$Pr), 3.71 (br t, J=4.6 Hz, 2H, CH$_2$NH).

Example 2

Synthesis of Bradsyl-Labeled Chitosan

To synthesize the Bradsyl-labeled chitosan compound, the chitosan is preferably solubilized in an acid such as acetic acid or lactic acid. For example, 2 g of chitosan (Sigma, St. Louis, Mo.) and 40 mL of 10% acetic acid were combined and the chitosan was allowed to solubilize overnight.

Next, 100 mg of the naphthalimide, such as Bradsyl, was dissolved in 1 mL of acetone or DMSO. The naphthalimide solution was then added slowly, with stirring, to the chitosan solution. If it is added too quickly, the chitosan will precipitate. Immediately after adding the naphthalimide, 6 M KOH was added slowly, with stirring, until the pH of the solution was about 8 to about 9 as tested by pH paper. If the target pH was exceeded, back titration was not performed. The pH was monitored over the course of about 3 to about 4 hours, adding more base as necessary to keep the pH between 8 and 9. The mixture was allowed to stir at this pH overnight.

Then, 100 mL of 10% acetic acid was added. The solution was stirred until the modified chitosan was completely dissolved, or for at least two hours. The solution was centrifuged and any insoluble material was discarded. The insoluble material consists of excess naphthalimide and insoluble or overmodified chitosan.

To purify the solution by alkaline precipitation, 6 M KOH was added to the supernatant until the pH was about 8 to about 9. The modified chitosan was allowed to precipitate for at least thirty minutes. The precipitate was then collected via centrifugation.

Finally, the modified chitosan solution was added to dialysis tubing with a syringe and both ends of the tubing were tied off. The dialysis tubing was placed in a 1 L Erlenmeyer flask and about 1 L of 10% acetic acid was added. The sample was dialyzed until all of the chitosan had resolubilized, or for at least 12 hours. The dialyzate solution was discarded after noting the color and replaced with 1 L of deionized water. After 12 hours the dialyzate solution was replaced with fresh deionized water and was dialyzed for an additional 12 hours. Finally the sample was dialyzed against phosphate buffered saline ("PBS") for 24 hours.

The concentration of chitosan in the homogenous modified mixture was determined by taking an aliquot, typically 1 mL, and determining the weight. This sample was then dried and the residue weighted. The resulting data (mass chitosan/mass sample) yielded the concentration of solids, typically expressed as mg/g. Samples with chitosan concentrations between 1 and 100 mg/g have shown effective bonding. Samples with chitosan concentrations between 10 and 50 mg/g have shown the greatest efficacy.

The modification ratio of Bradsyl Chitosan was determined by taking a 1.00 mL aliquot and diluting it to 25.00 mL with 10% acetic acid. The optical absorbance was measured at 450 nm. After correction for dilution, a molar extinction coefficient of 20,000M$^{-1}$ cm$^{-1}$ was used to determine the naphthalimide concentration in the sample. The mass of chitosan in the sample was used to determine the concentration of sugar subunits, using a molar equivalent weight of 180 g/mole. The modification ratio was expressed as a ratio of sugar subunits to bound naphthalimide groups. A larger number indicates a lower level of modification. A Bradsyl chitosan with a modification ratio of at least 1500 (1 naphthalimide per 1500 sugars) has been shown to be effective in tissue bonding. Better results are obtained with a modification ratio of at least 500. The best results are obtained with a modification ratio of at least 100.

Example 3

Synthesis of Labeled Chitosan

Standard amide coupling reactions were used to attach various naphthalimides to chitosan.

Figure 19:
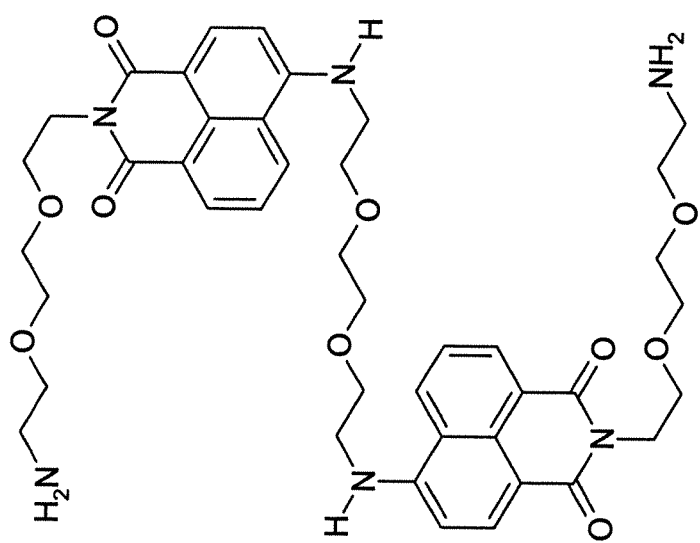
FIG. 19 shows an example of a dimeric hydrophilic 4-amino-1,8-naphthalimide compound.

Two grams of chitosan (Sigma) were dissolved in 40 mL of 8% acetic acid. This solution was diluted with 160 mL of methanol and treated with 1.4 g of succinic anhydride dissolved in 50 mL of acetone. This succinylated chitosan is purified by repeated basic precipitation followed by solubilization in 0.1 M HCl. The naphthalimide was attached to the chitosan using cardodiimide-mediated coupling reactions. A saturated chitosan in 0.1 M HCl solution was diluted five-fold with methanol and an amine terminated naphthalimide (having the structure shown in FIG. 19) was added to this solution. The addition of a coupling reagent (N-ethyl-N'-(3-dimethylaminopropyl)-carbodiimide hydrochloride) resulted in the covalent attachment of the naphthalimide. This modified chitosan was purified by either repeated extractions with DMF or by repeated basic precipitation followed by solubilization in 0.1 M HCl.

Example 4

Cross-Linking of the Naphthalimide-Chitosan Species

Studies were performed to determine if cross-linking occurred within the naphthalimide-chitosan gel after photoactivation. The gel was formed by solubilizing chitosan (Biopolymer Engineering, Inc., Eagan, Minn.) in PBS at 25 mg/mL, then making a 1:4 dilution. Free naphthalimide compound (having the structure shown in FIG. 19) was added to make an 8 mM concentration. Next, 20 μL aliquots of this solution were dispensed on clean glass microscope slides. A group of these slides were then exposed to activating blue light (800 mW/cm$^2$) for 7 minutes. A control group of slides was maintained in the dark until air-dried. 200 μL of H$_2$OD was used to rehydrate the solutions. While all of the controls quickly went back into solution, the specimens containing the naphthalimide and exposed to the activating blue light formed distinct and durable films which did not redissolve in water.

The films of the treated specimens were also subjected to agitation, acetate buffer, 1% SDS, and H$_2$OD at pH 4 and 6. The cross-linked chitosan films maintained their configuration even after a week or longer in the various solutions. Observed under the microscope, these films had a very distinct appearance with crystalline-like features. The control specimens did not show these features.

Aggregate formation was also detected chromatographically in a naphthalimide-modified chitosan solution that had been exposed to room light only, rather than a filtered arc lamp light source. Liquid chromatography produced three distinct peaks. The peak at about 1500 seconds was indicative of native chitosan materials, while the peaks at shorter time periods represented larger aggregate molecules formed by naphthalimide-induced photochemical cross-linking.

Example 5

Effects of Light Exposure on Tissue Bonding

Figure 10:
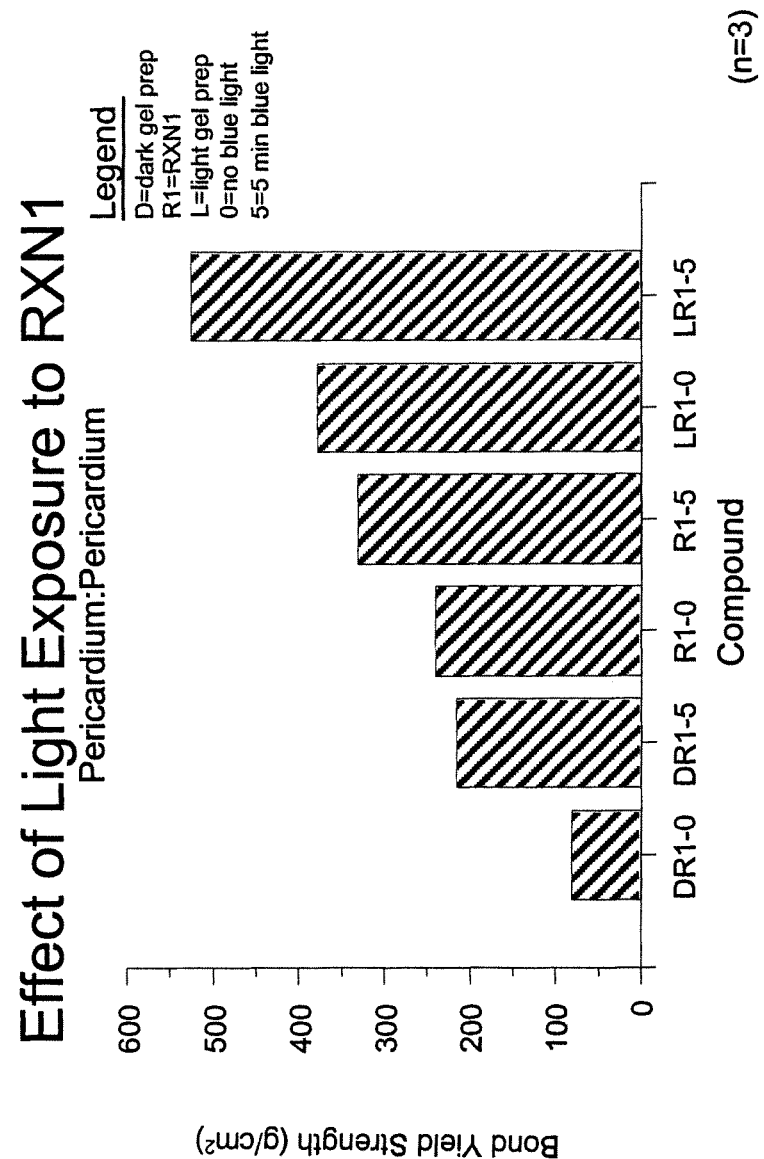
FIG. 10 shows the effects of various amounts of light activation on bond strengths between pericardium tissue samples bonded with a naphthalimide-labeled compound.
Figure 20:
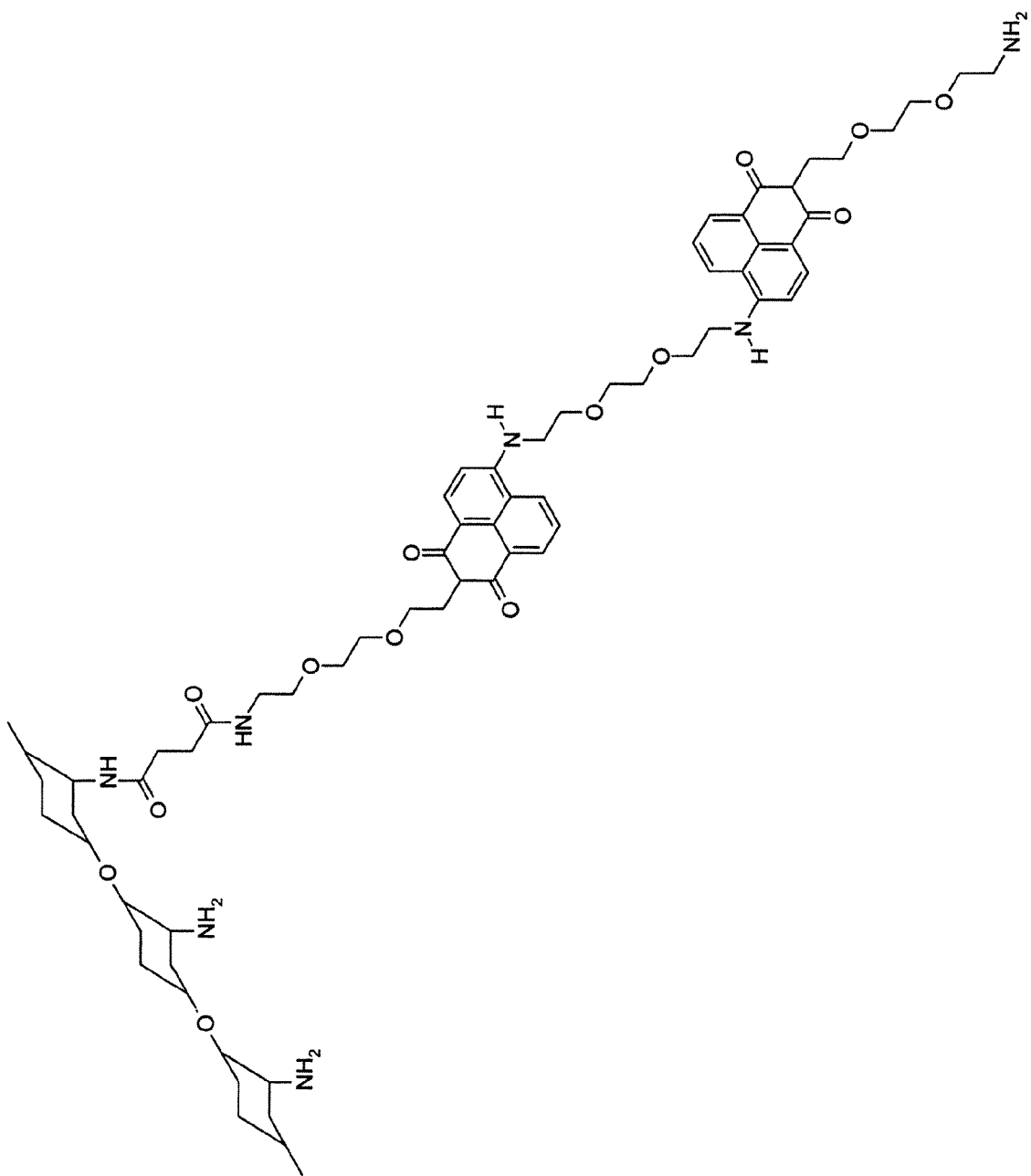
FIG. 20 shows an example of a naphthalimide-labeled biomolecule.

An example of the naphthalimide-labeled chitosan (having the structure shown in FIG. 20) also demonstrated an ability to bond tissues under "dark" conditions, or having been exposed only to room light during synthesis and procedures, rather than blue light irradiation. FIG. 10 shows the results using various amounts of light activation. The naphthalimide-labeled compound was designated RXN1.

A screening model of swine pericardium was used. The pericardium has been identified as a potential biological patch material for arterial repair. This highly collagenous tissue is thin and fairly translucent, therefore optimizing the potential for light penetration, while also being durable and readily available.

A thin film of the experimental naphthalimide-chitosan formulation (20 μL) was applied to the pericardium. Some compound samples were prepared entirely in red light, a wavelength at which there is no absorption by naphthalimide, and thus were prepared effectively in the dark (D). Others were prepared in ambient laboratory light, and others were subjected to 5 minutes of blue light irradiation at 800 mW/cm$^2$ prior to tissue application (L). The pericardial patch segment was then opposed to the treated tissue in an area of overlap with single-thickness "tails" projecting from each end. Some tissue samples were then subjected to an additional 5 minutes of blue light irradiation (−5). All samples were clamped at 5 kg/cm$^2$ for 5 minutes. After the tissues were bonded, the tissues were carefully placed in PBS for at least an hour prior to tensile strength testing to ensure any residual "stickiness" resulting from partial dehydration would not influence the measured tensile strengths. Testing of tensile bond strengths was conducted using an incremental loading system, whereby the force was gradually increased to the point of bond failure. Peak loads were noted and bond strengths were calculated as g/cm$^2$.

The bond formed in ambient laboratory light but the absence of arc lamp exposure (R1-0) showed significant strength when compared to the bond formed in ambient light with arc lamp exposure (R1-5). In particular, the bond formed in the absence of arc lamp exposure had approximately 73% of the strength of the light exposed bond. Exposure of the compounds to 5 minutes of blue light irradiation at 800 mW/cm$^2$ prior to tissue application, followed by subsequent clamping at 5 kg/cm$^2$ for 5 minutes without arc light exposure to the clamped tissues, produced higher bond strength (LR1-0), approximately 58% greater than that of the bonds prepared in ambient light alone (R1-0). The strongest bonds were obtained when the compounds were activated prior to application and the tissue was irradiated afterward as well (LR1-5).

Solutions and tissue bonds that were protected from room light activation entirely (DR1-0) consistently showed the lowest bond strengths. However, light exposure of 5 minutes at 800 mW/cm$^2$ produced an approximate 50% increase in bond strength (DR1-5).

The results indicate that both incidental lab light exposure and controlled blue light exposure prior to application of the bonding gel to the tissue can produce improvements in bond strengths, eliminating the requirement that tissues be irradiated during the bonding procedure.

Example 6

Tissue Bonding with Varying Light and Pressure

Figure 11:
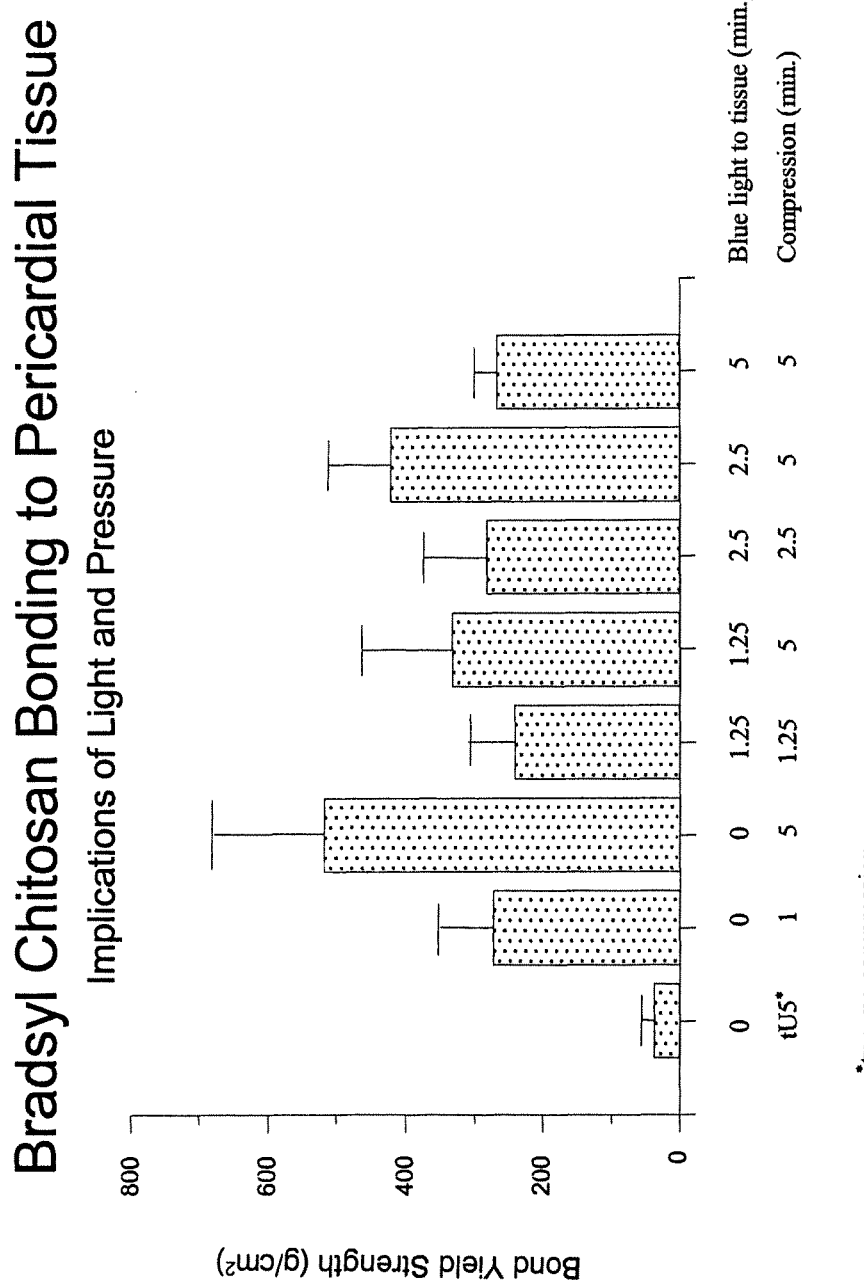
FIG. 11 shows the effects of various amounts of light activation and compression on bond strengths between pericardium tissue samples bonded with a naphthalimide-labeled compound.

Bradsyl-labeled chitosan exposed only to ambient laboratory light during synthesis and experimental manipulations, was used. The bonding procedure was substantially the same as that described in Example 5, using alkylated bovine pericardium (Veritas™ sheets, Synovis Surgical, St. Paul, Minn.). Results are shown in FIG. 11. The sample in which no external pressure was applied to the lapped joint (tu-5) showed poor bond yield strengths. The addition of the weight of a single glass slide, about 0.025 kg/cm$^2$, which ensured apposition of the tissues, substantially improved performance. Mean bond strength nearly doubled between one minute and five minutes of this minimal compression.

Blue light irradiation of the tissue samples, ranging from 1.25 to 5 minutes at 800 mW/cm$^2$, appeared to consistently reduce bond strength when compared to samples with the same compression time. Without wanting to be bound by theory, it is likely that ambient light prior to tissue application produces chemical species in the adhesive compound that cause subsequent bonding in the tissue environment. Additional intense blue light appeared to destroy these productive bonds or deplete the chemical species.

Example 7

Tissue Bonding in Arterial Repair

Figure 12:
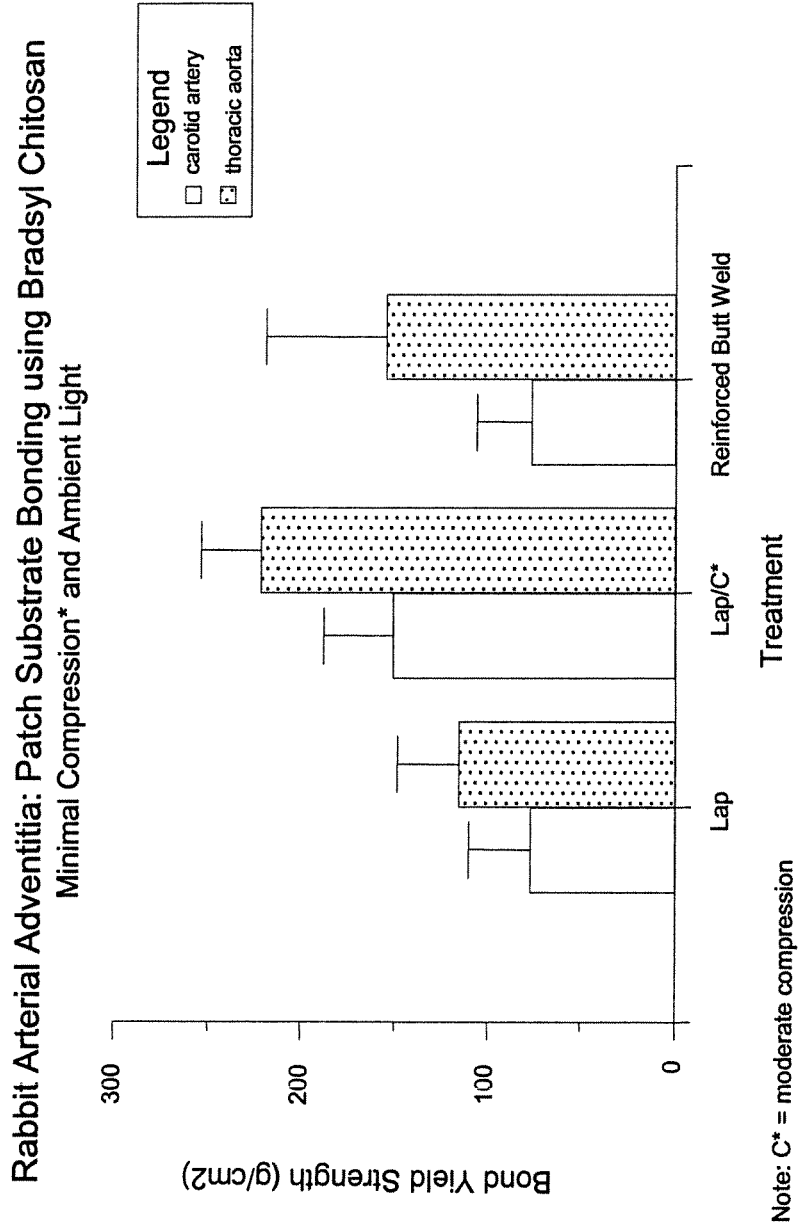
FIG. 12 shows the bond strengths with various amounts of compression between pericardium tissue samples and sections of carotid artery and thoracic aorta.

The Bradsyl chitosan adhesive was also tested in adhering a bovine pericardial patch (Veritas™, Synovis Surgical, St. Paul, Minn.) to the adventitia or outer surface of the thoracic aorta and carotid artery of rabbits. The procedure described in Example 3 above was used. One sample was tested with minimal compression, or with an overlying glass slide to impose about 0.025 kg/cm$^2$ pressure on the bond area for about 5 minutes without any direct blue light illumination of the tissue bonding region. Another sample was subjected to moderate compression, by compressing the tissue between two glass slides with rubber bands, which is estimated to be about 1 kg/cm² pressure. A third sample used a patch overlying arterial wall sheets opposed as a butt weld. As seen in FIG. 12, with moderate compression, lap bond strengths of up to about 0.225 kg/cm² were formed for the thoracic aorta and about 0.150 kg/cm² were formed for the carotid artery. Bond strengths using the reinforced butt weld were about 0.150 kg/cm² and 0.075 kg/cm² for the thoracic aorta and carotid artery, respectively. The thoracic aorta bonds were consistently stronger than those of the carotid artery. Furthermore, moderate compression appeared beneficial.

While these overall bond strengths were notably lower than those observed in pericardium-pericardium tissue bonds, they still provide significant adherence of the patch to arterial adventitia. Thus, the results support the application of the Bradsyl chitosan gel, with lab light exposure, in arterial patching. The application is particularly supported for smaller arteries, with a diameter of about 3 mm or less, for which tangential wall hoop stress value calculations of less than 0.15 kg/cm² from an internal pressure of 300 mmHg is less than the values realized in the above patch-arterial adventitia bonds. The Bradsyl chitosan gel is therefore useful in the sutureless repair of smaller blood vessels.

Example 8

Cytotoxicity Testing of Bradsyl Chitosan Gel

The primary limitations of current bio-adhesives lie either in insufficient bond strengths or toxicity issues. While the Bradsyl chitosan adhesives demonstrate excellent bond strength and reproducibility, these new formulations were also subjected to toxicity testing. Cytotoxicity was assessed using a cell culture model. Two cell lines were exposed to varying doses of the adhesives. Cell viability was measured using the MTT (tetrazolium salts) spectroscopic light absorption based assay. Control wells were also prepared to determine relative toxicity.

Figure 13:
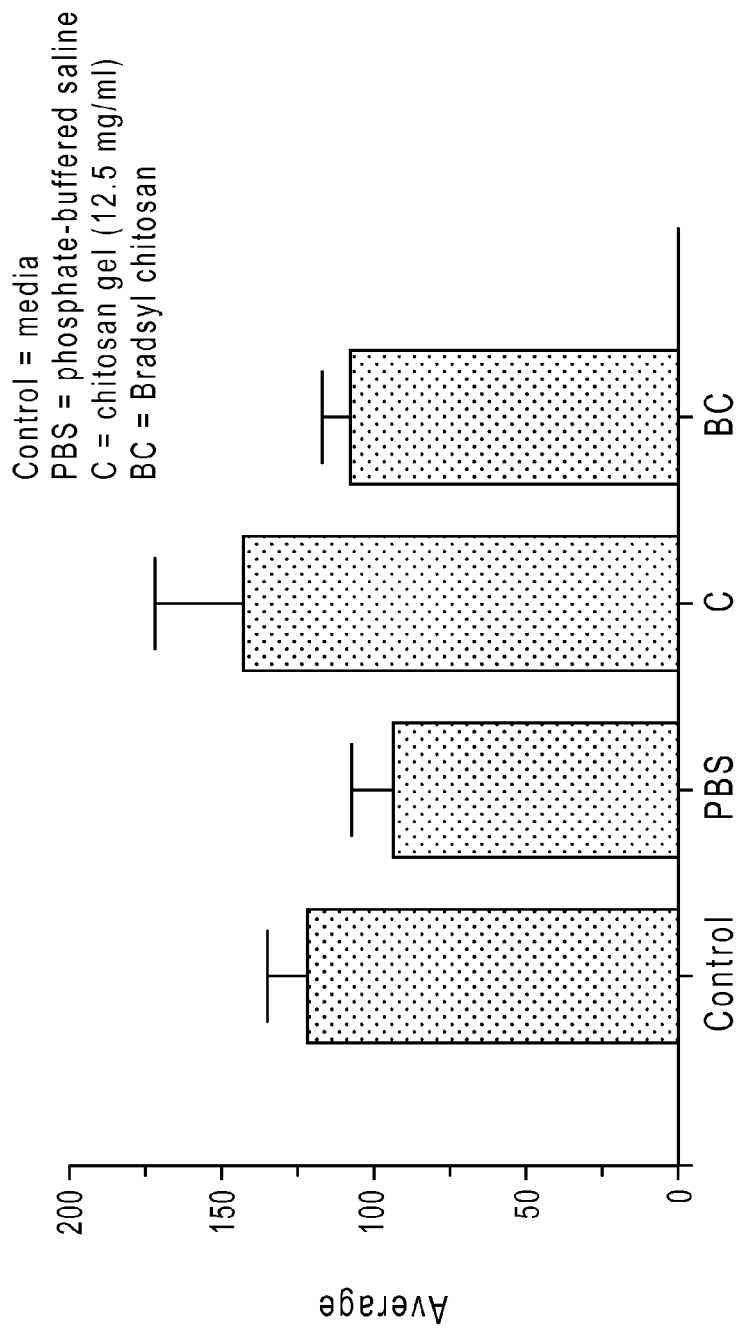
FIG. 13 shows the viability of vascular smooth muscle cells exposed to supraphysiological doses of chitosan and a naphthalimide-labeled compound.
Figure 14:
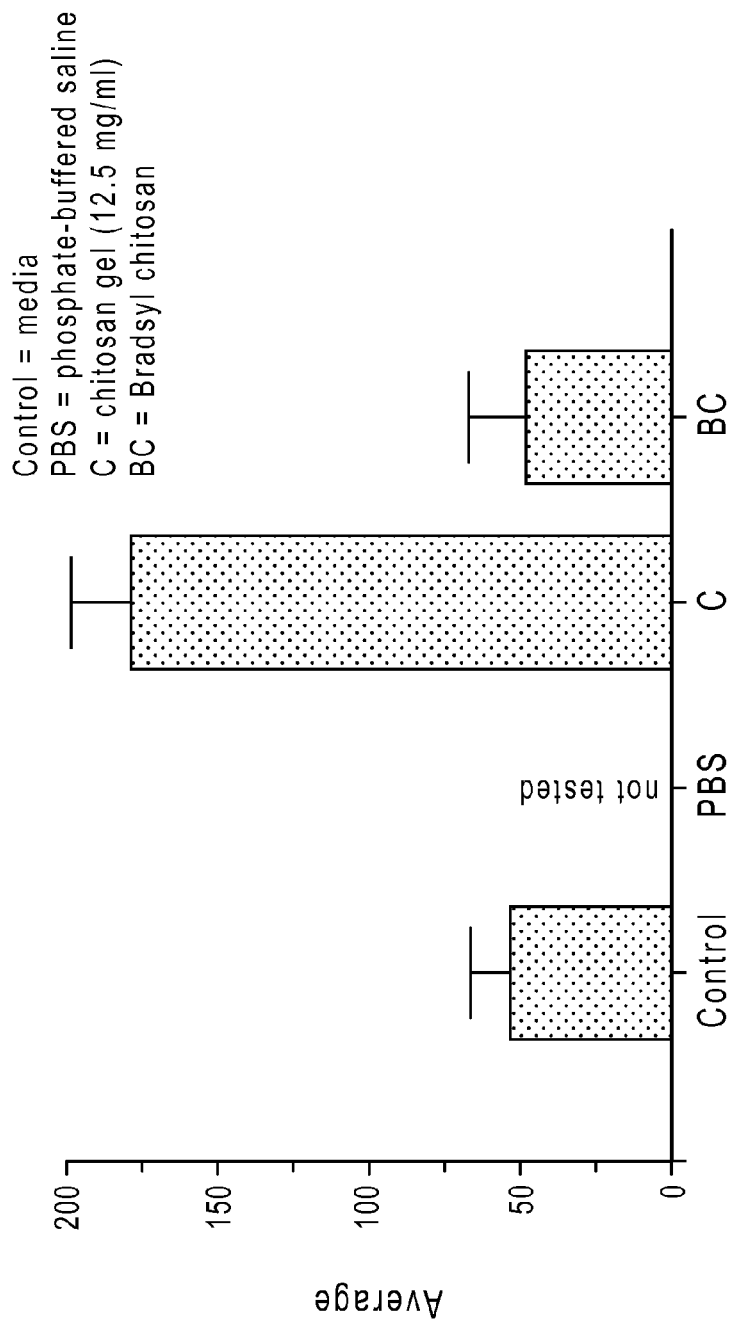
FIG. 14 shows the viability of human umbilical vein endothelial cells exposed to supraphysiological doses of chitosan and a naphthalimide-labeled compound.

The results, shown in FIGS. 13 and 14 were obtained in cultured vascular smooth muscle cells ("VSMCs") (FIG. 13) and endothelial cells ("ECs") (FIG. 14). These cell lines showed varying degrees of sensitivity to the adhesive when exposed to 40 μL of the test compound in 100 μL of media for two days. The 40 μL amount of the test compound was chosen because it represents the amount of adhesive used per unit area that is applied during the ex vivo tissue bonding protocol. This does not account for run-off and displacement as the tissues are overlapped and compressed. Furthermore, during tissue bonding, only the surface cells are directly exposed. Subsequent layers are exposed by diffusion at lower doses. Therefore, the cytotoxicity tests represent the cellular response to supraphysiological doses with direct cell contact.

The addition of 12.5 mg/mL chitosan gel alone appears to have no deleterious effects on cell viability. Indeed, chitosan showed a tendency to enhance growth, particularly in ECs, with a 354% increase over the controls. This feature is advantageous in wound repair. The Bradsyl chitosan results were comparable to control wells exposed to media alone or 40 μl of PBS in 100 μl media, demonstrating that the formulation is relatively innocuous with regard to cellular toxicity. Because these compounds do not require blue light activation subsequent to tissue application, this variable was not tested. This feature of the Bradsyl-labeled compounds preserves tissues from any cell-damaging blue light toxicities. Thus, even at supraphysiological doses, the Bradsyl-labeled compounds demonstrate high bond strengths and a promising biocompatibility profile, which furthers their applications in soft tissue bonding and wound closure.

Example 9

In Vitro and In Vivo Arterial Patching

In vitro patch repairs were performed on euthanized rabbit aorta segments in an organ chamber using Bradsyl-labeled chitosan, under protocol approved by the University of South Dakota Institutional Animal Care and Use Committee, and essentially as described in Example 3 above. A puncture wound was made through the arterial wall of the arterial segments. Following deposition of 20 μL of the adhesive gel to the arterial surface (Veritas™, Synovis Surgical, St. Paul, Minn.), the patch and arterial surfaces were apposed with gentle molding of the patch outer surface to conform to the outer cylindrical surface of the infolded arterial segment. The estimated pressure was approximately 0.025 kg/cm². The gentle molding contact was maintained for 5 minutes, with all of the patch surface contacted.

Although bulging of the patch over the puncture wound was noted, patch segments withstood intraluminal pressures exceeding 1200 mmHg before leakage was observed.

In vivo testing of the patch was also performed under the review of the University of South Dakota Institutional Animal Care and Use Committee. After the animals were anesthetized, the abdominal aorta was exposed between the renal arteries and the aorto-iliac bifurcation and temporarily clamped. A forceps was used to pinch and lift the aorta while small scissors were used to make a 3 mm longitudinal, irregular opening. This was sealed as described in the in vitro study. After 5 minutes of bonding time, the clamps were removed, allowing the return of blood flow and pressure. In all animals tested (n=6), no bleeding was observed during the subsequent observation under anesthesia (about 30 minutes). Following each experiment the animal was euthanized according to the approved protocol.

The results support the use of the Bradsyl chitosan gel in vascular repair.

Example 10

Fabrication of a Tubular Vascular Graft

The following experiments were designed to explore the application of the Bradsyl chitosan technology to fabrication of collagenous biomaterial prostheses, 3 dimensional shaping, bonding, and sealing of a tubular form of pericardium (Veritas™, Synovis Surgical, St. Paul, Minn.). Sheets of the pericardium, approximately 4 cm wide with varying lengths, were rolled up on a wooden mandril having an outer diameter of about 8 mm. This resulted in a tube 4 cm in length with an 8 mm diameter and overlap regions of 10, 20, or 30 mm, to which the Bradsyl-labeled chitosan adhesive was applied. After removal of the mandril, these tubes were mounted in an organ chamber for subsequent burst pressure testing. Regardless of overlap area, average burst pressures of approximately 250 mmHg were observed.

Another approach to the fabrication of a tubular vascular graft involves the homogenization of a purified, acellular collagen matrix (Veritas™, Synovis Surgical, St. Paul, Minn.). Preliminary experimentation used Bradsyl chitosan (10 mg/mL) to cross-link Veritas™ homogenate at a 1:1 ratio of adhesive to homogenate. This resulted in definitive cross-linking of the homogenate, with the cross-linked material retaining cohesiveness over the course of 8-12 days in PBS at pH 7.4, while uncross-linked controls completely disassociated upon rehydration. The Bradsyl chitosan technology can be employed to crosslink the tissue homogenate into desired cylindrical conformations of varying diameters, with or without bifurcations or other prosthetic design.

Example 11

Naphthalimide Compound Penetration of Atheromatous Arterial Tissue

The following experiment was performed to analyze the compound form, compound concentration, and compound exposure time that provide adequate tissue penetration for expanded arterial stabilization.

Figure 21:
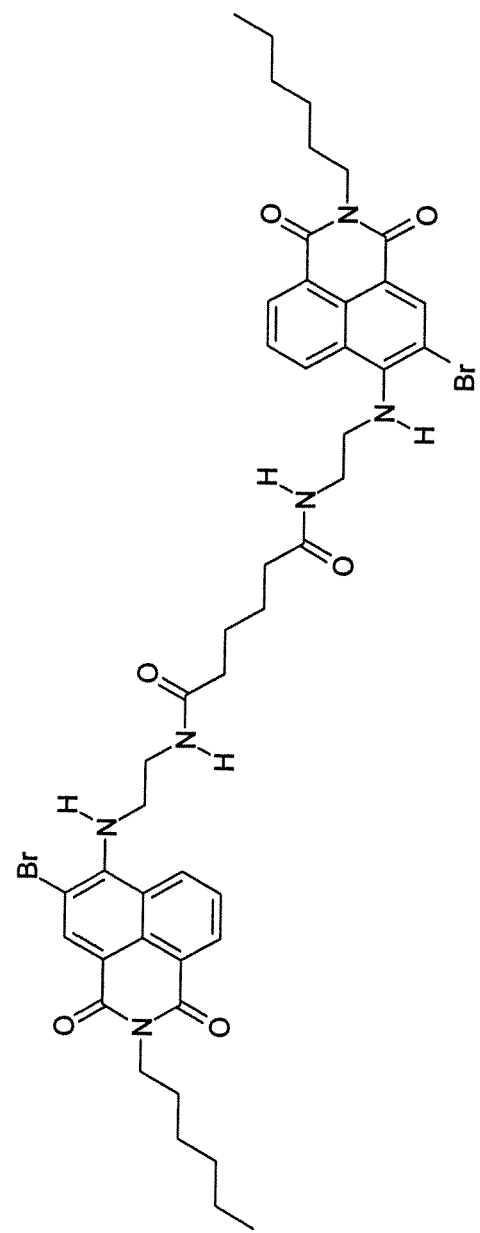
FIG. 21 shows an example of a dimeric lipophilic 4-amino-1,8-naphthalimide compound.
Figure 22:
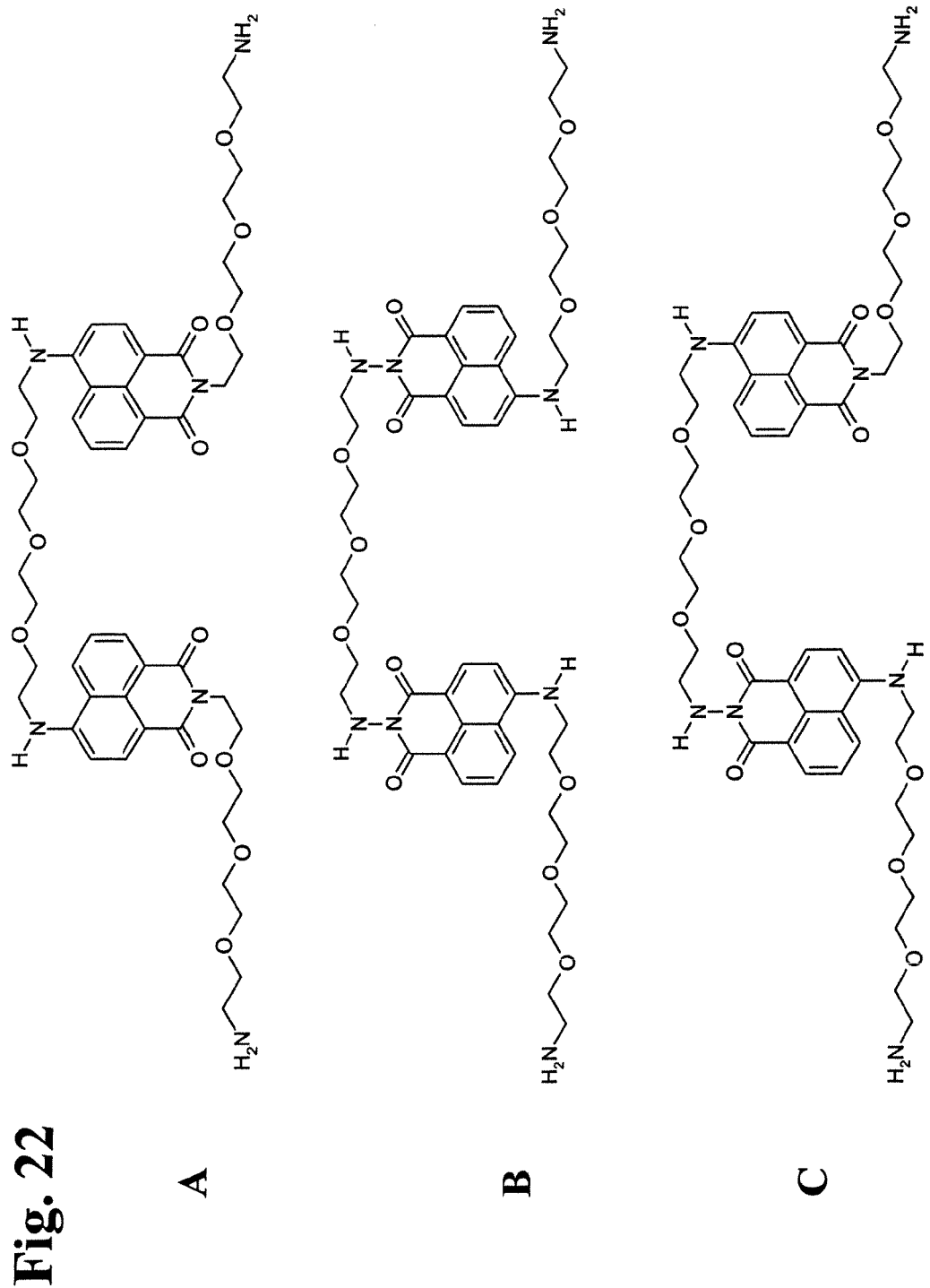
FIG. 22 shows examples of three isomers (A, B, and C) of a dimeric hydrophilic 4-amino-1,8-naphthalimide compound.

These experiments utilized atherotic carotid artery from young adult (3-6 months) male New Zealand White rabbits. Atherosclerotic lesions were created using the air-desiccation model (LeVeen, 1982). Approximately 4 cm lengths of both the right and left carotid artery were harvested from donor animals. These segments were opened longitudinally and divided into 8 small rectangles, which provided 16 test segments from each animal. These arterial pieces were immersed in high or low concentrations of a solution of a lipophilic naphthalimide compound (having the structure shown in FIG. 21) or a solution of a hydrophilic naphthalimide compound (a mixture of the three isomers A, B, and C shown in FIG. 22) for periods of either 5, 15, or 30 minutes. The lipophilic naphthalimide was dissolved in 20% Cremophor® EL (BASF, Mount Olive, N.J.), a lipophilic solvent and micellar agent, to provide an aqueous stock solution (0.9 mM, determined via optical density). The hydrophilic bis-naphthalimide solution was dissolved in PBS, a hydrophilic solvent (0.9 mM solution). Solvent controls included PBS and Cremophor®. "Low" concentrations were made by making a 1:2 dilution of the stock solution.

Following incubation in solution, artery segments were frozen in liquid nitrogen, cryosectioned and examined by confocal microscopy. Images were analyzed using commercial image analysis software. Fluorescent profiles emitted by the incorporated naphthalimide compounds were used to determine an average intensity and the depth of compound penetration. Because each animal provided sufficient tissue to contribute to all experimental groups, a paired statistical design was utilized for data analysis. Because of the heterogeneity of variance, the Friedman statistic was used, followed by a modified Student Newman Keul's multiple comparison test.

Analysis of the results showed that immersion of the artery segments in hydrophilic compound, the bis-naphthalimide, resulted in compound penetration from the luminal side at all concentrations and exposure times tested. After 5 minutes of incubation time the low concentration had penetrated approximately 31% of the medial thickness compared to 41% with the high concentration. After 15 minutes, the low and high concentrations penetrated 54% and 80% respectively. After 30 minutes of immersion, the low and high concentrations penetrated 77% and 100% respectively with the high concentration at 30 minutes penetrating beyond the medial wall into the outer adventitial layer, a cumulative penetration of 129%.

The lipophilic compound penetration and localization in the atheromatous vascular wall segment differed markedly from the hydrophilic form, with the former being localized primarily in the adventitial wall component (increasing with time and concentration) rather than within the media. Maintenance of compression of this wall component is unimportant in the stabilization of luminal patency following balloon dilation. Controls showed virtually no fluorescence after autofluorescence was filtered out.

The results indicated that the naphthalimide compounds were taken up by the arterial wall.

Example 12

Tissue Bonding in Atheromatous Arterial Tissue

The following experiment was performed to examine whether, upon adequate compound exposure and radiation, sufficient molecular interaction would occur between apposed luminal surfaces of atherosclerotic rabbit carotid artery to cause a significant increase in the strength of bonds over controls.

Rabbit carotid arteries were lesioned and dissected as described in Example 11 above. Isolated arterial segments were catheterized with a 3.0 mm balloon catheter and subjected to a standardized balloon inflation protocol (3 inflations to 6 atm with 30 second inflation ramps and one minute inflations with a one minute rest period between inflations). This protocol was used to produce arterial injury that may be characteristic of that observed post-angioplasty in vivo. Each artery was opened longitudinally, with each rectangle cut into four pieces, yielding a total of eight tissue segments from each animal. In this manner, each animal contributed to one experimental and three control groups allowing for a paired statistical design.

The experimental group was prepared by immersing the segments in hydrophilic compound solution (same solution used in Example 11, at a concentration of 0.9 mM) for 30 minutes. Two saturated arterial segments were positioned so that the luminal surfaces were apposed in an area of overlap, with single thickness "tails" projecting from each end. The tissue prep was wrapped in a thin polyurethane sheet, sandwiched between glass microscope slides, and clamped with thin C-shaped spring steel clips. Based upon spring-load deflection calibration, the resultant pressure was estimated at 3 $kg/cm^2$, sufficient to bring tissue in close apposition. The tissue was then exposed to 400-500 nm wavelength light from a 159 W arc lamp for 30 minutes at an intensity of 800 $mW/cm^2$. The dilating force of a polyethylene balloon catheter at 6 atm is approximately 15.75 $kg/cm^2$, which provides sufficient pressure to appose surfaces within wall and plaque by balloon dilation.

Control groups consisted of atheromatous sheets soaked with naphthalimide solution, clamped and held in the dark, and sheets painted with naphthalimide-free PBS and held in the dark or irradiated. Solution temperatures were held at 27° C.

Following light exposure or equal dark holding times, tissue was unclamped and removed from the polyurethane. Samples were rehydrated in saline prior to testing of tensile strengths (Sintech instrumentation). Pneumatic grips secured the single thickness "tails" of the overlapped tissue segments. The grips were then progressively separated mechanically to increase tension in the area of overlap. Computer generated graphs of the stress load yielded the peak stress achieved prior to separation of the apposing surfaces. The Friedman statistic and modified Student Neuman Keul's multiple comparison statistical tests were used for analysis.

Control groups consistently failed, with values no higher than 0.035 $kg/cm^2$, while the hydrophilic dimeric 1,8-naphthalimide (MBM Gold 12-11-12, MicroBioMed. Corp., Dallas, Tex.) yielded bond strengths averaging 0.07 $kg/cm^2$ for the arterial wall segments. Subsequent experimentation with thoracic aorta segments yielded bond strengths of 0.122 kg/cm$^2$.

The results indicate that cross-linking does occur between protein constituents of the arterial wall, which is necessary to maintain the expanded diameter and repair intimal and medial dissection, thus limiting a proliferative reparative response and ultimately restenosis.

Example 13

In Vitro Stabilization of Dilated Artery Wall Dimensions

The following experiment used intact cylindrical arterial segments perfused in an organ chamber to more closely simulate in vivo conditions. The organ chamber was equipped with a dissecting scope, video camera, and VCR to enable magnified views of the artery and to store images for later review. The ability of the technique to repair angioplasty-induced intimal and medial dissections was evaluated from histological analysis.

Rabbit carotid arteries were lesioned as described in Example 11, except that a more discrete lesion (approximately 1 cm) was produced. After 4-6 weeks of plaque development, the carotids were dissected and excised as in Example 11. The isolated 4 cm arterial segment was mounted in a specialized organ chamber by cannulating both arterial ends with tubing through which 37° C. physiological saline solution perfusate was circulated using a diaphragm metering pump to maintain oxygenated perfusate solution and nutrient supply. A 95% oxygen/5% carbon dioxide gas mixture was bubbled into the saline solution reservoir to generate oxygenated perfusate. The segment was anchored to maintain its in situ length. Following mounting of the artery the vessel was perfused for 30 minutes to allow the arterial tissue to equilibrate. Intraluminal pressures were measured continuously using a computer-based physiograph.

Each arterial segment then underwent a standardized balloon inflation to simulate PTCA. Balloon diameters were chosen to approximate a 1.3:1.0 ratio of maximal balloon diameter to "normal" vessel diameter. The balloon catheter was introduced into the vessel lumen via a permeable septum perforated by an introducer/sheath that accommodates the balloon catheter shaft. The catheter was advanced until the 2 cm balloon bridged the center portion of the arterial segment. The standard angioplasty protocol included three inflations to 6 atm with 30-second inflation ramps and 60 second inflations. Each inflation was ended by free release of the inflation mechanism followed by 30 seconds to monitor baseline pressures. Video recording was continuous throughout. External diameter changes were recorded using edge detection software.

After balloon dilation, experimental arteries were filled with 12 mM hydrophilic naphthalimide compound for 30 minutes to ensure diffusion of the compound into the tissue. A final single inflation was performed. The arterial segment was irradiated with 800 mW/cm$^2$ for a total of 45 minutes during balloon inflation, with the artery being rotated twice to ensure irradiation of the entire arterial circumference. Intraluminal irradiation via a fiber optic guidewire would improve uniformity of light delivery and reduce required irradiation times. Technology is currently available to provide intraluminal light delivery.

Control groups consisted of a group with no irradiation, a group with naphthalimide without irradiation, and a group with saline instead of naphthalimide compound.

After treatment, the perfusion solution was changed to phosphate buffered glutaraldehyde, tissues were perfused, and tissues were subsequently stored in the same solution to fix the tissue for light and electron microscopic analysis.

Histologic and morphometric analyses consisted primarily of (1) determination of cross-sectional area, medial area, intimal area, and percent plaque, and (2) determination of luminal circumference and external medial circumference and other physical dimensions as well as histologic evaluation of tissue injury. The morphometric analyses quantified luminal, plaque, and medial areas on perfusion-fixed treated and control arteries.

Figure 15:
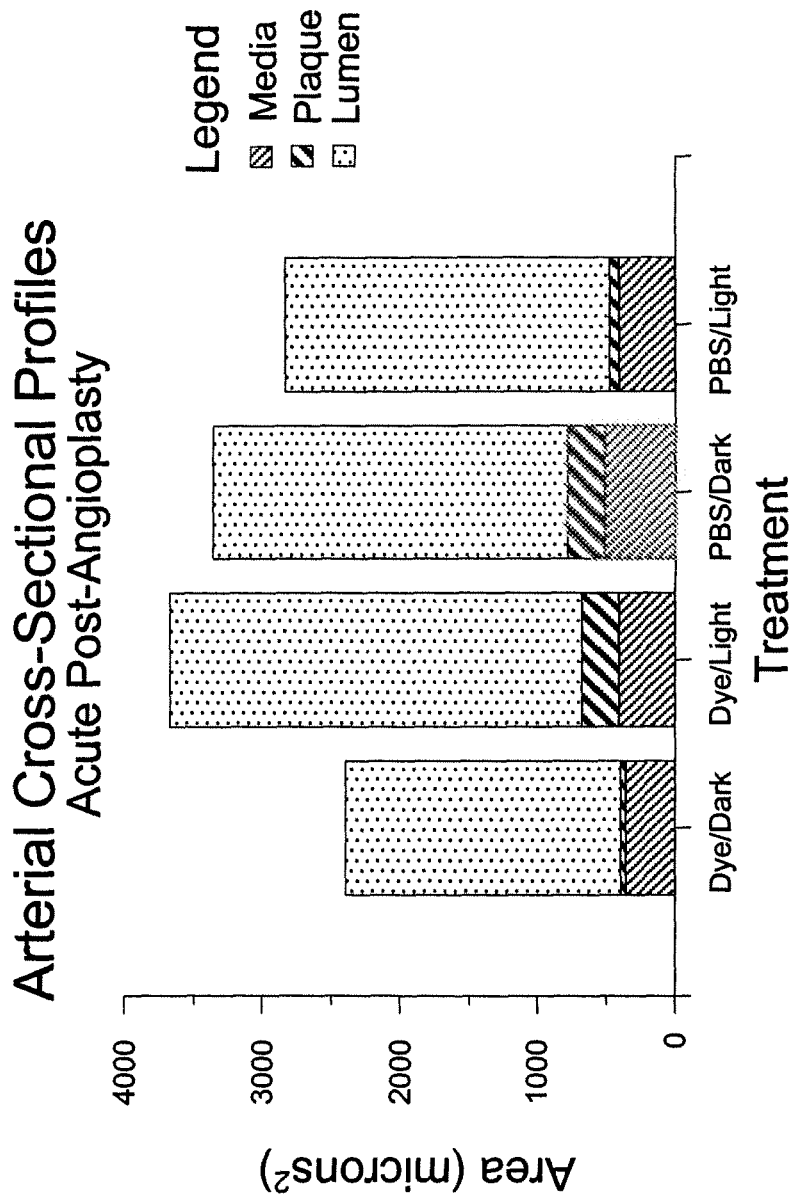
FIG. 15 shows the cross-sectional profiles of viable arterial segments subjected to simulated repair of post-angioplasty vascular injury and stabilization of the expanded arterial diameter by a naphthalimide compound.

Considerable variability was observed in the extent of plaque found in the segments independent of group. Although this variability made morphometric analyses, shown in FIG. 15, more difficult, there was a strong trend for medial thinning in the naphthalimide/light group. The medial thickness represented 5.5%±2.2% of the outer radius versus 9.2%±2.2% in the PBS/dark group. Luminal areas tended to be larger in photochemical and light treated groups.

The results indicate that stabilization of the dilated lumen dimensional area by photochemical means does occur, creating an endogenous "stent."

Example 14

Retention of Compressed Arterial Wall by Cross-Linking

Compression of the atherosclerotic plaque and other tissue components should result in gain in lumen diameter. Example 13 showed medial wall thinning and gain in lumen diameter following photochemical bonding in the dilated state. Furthermore, previous experiments with compressed overlapped skin painted with naphthalimide and irradiated showed stabilization of the compressed skin, with the thickness equals to 70% of that of uncompressed skin. The following experiment was done to determine if similar retention of tissue compression was observed in vascular tissue.

Swine coronary arteries were dissected from fresh postmortem swine hearts. Each artery was opened longitudinally and 3 mm discs were obtained using a biopsy punch.

The experimental group (naphthalimide/light) was prepared by immersing the discs into hydrophilic compound solution (15 mM MBM 10-8-10, MicroBioMed. Corp., Dallas, Tex., a mixture of 3 dimeric isomers) for 5 minutes. The disc was then wrapped in a polyurethane sheet, sandwiched between glass microscope slides, and positioned in a lever device designed to apply controlled force to the slide surface. Weights of 5.3, 10.14, and 20.28 kg/cm$^2$ were applied. Light at wavelengths 400-500 nm from an arc lamp was delivered to the specimen surface at an intensity of 800 mW/cm$^2$ for 10 minutes. Control groups consisted of naphthalimide treated discs with no light irradiation and discs exposed to buffered saline solutions with no naphthalimide, either exposed to light or kept in the dark.

Following light exposure or equal dark holding times, the tissue was removed from the pressure device and wrapping film and hydrated in phosphate buffered saline for twenty hours prior to final diameter measurements, to ensure any retention of compression was not due to partial dehydration. Diameter measurements were made prior to any compression, immediately following treatment (prior to re-hydration) and 20 hours after re-hydration. Friedman statistics and Student Neuman Keul's multiple comparison tests were used for data analysis.

The lower compressive force of 5.34 kg/cm$^2$ showed significant compression of the segments and after the 20 hour re-hydration period, the naphthalimide/light treated group showed significantly greater residual compression compared to controls (i.e., naphthalimide/light group—19.4±8.4% vs. naphthalimide/dark group—7.1±5.7%). The higher compressive forces proved to be too high for practical use as all higher forces caused wall damage and irreversible wall distortion. The lower force used was comparable with values that can be attained with balloon dilation.

The results indicate that photochemical cross-linking of vascular wall constituents during compression can result in a significant retention of wall compression before and following re-hydration.

Example 15

Intraluminal Delivery of Naphthalimides

In this experiment, intraluminal delivery via catheter and reperfusion washout of these naphthalimide compounds was evaluated to determine their efficacy for bonding the vascular wall.

Local delivery of these 1,8-naphthalimide compounds was achieved using a commercially available Coronary Infusion Catheter. (DISPATCH™, SciMed®, Maple Grove, Minn.). This catheter incorporates inflatable coils which create drug "compartments" that allow drug contact with the arterial wall. Its perfusion capability permits longer drug diffusion times without causing distal ischemia. This local delivery system allows for dwell times comparable to those used in previous in vitro experiments where successful compound penetration was demonstrated.

Normal carotid arteries were harvested from euthanized young adult (3-6 months) male New Zealand White rabbits for in vitro experimentation. A small length of artery was trimmed from each to serve as either untreated (negative) or immersion-soaked (positive) control tissue in subsequent fluorometric analyses. Arterial segments were catheterized and subjected to a standard angioplasty balloon protocol (described in Example 13) inflated to 6 atm for three one minute inflations while immersed in oxygenated physiological saline (PSS) solution at 37° C. The standard balloon catheter was then replaced with the DISPATCH™ infusion catheter, which was inflated to 6 atm pressure. The infusion port was loaded with 10 mM lipophilic (MBM Yellow 06-06, MicroBioMed. Corp., Dallas, Tex.) or hydrophilic 1,8-naphthalimide compound (MBM Gold 12-11-12, MicroBioMed. Corp., Dallas, Tex.) Three initial short, strong bursts were used to promote uniform filling of the "drug compartments." Subsequent infusion at 1.59 cc/hr maintained delivery of the compound over a 30 minute period. To ensure intraluminal delivery, arterial segments were suspended over a basin and continuously rinsed with saline rather than immersed to eliminate the potential of delivery of compound from any location except from within the lumen. Washout experiments were also performed in which PSS was perfused at physiological pressures for 10 minutes to evaluate compound retention. One of the control segments was immersed in the compound and used as a positive control.

All experimental arterial segments exposed to the naphthalimide compounds showed a yellow staining of the tissue visible by gross examination. A fluorometric assay was developed to quantify residual compound presence in the arterial wall. After a brief rinse and blotting, comparable weights of control and experimental tissue were homogenized (OMNI Tissue Homogenizer, OMNI International, Warrenton, Va.) in 4 mL of 0.9% NaCl. A standard curve was prepared using known compound concentrations. 40 µL of each of the unknown homogenates was added to 250 µL of 0.9% NaCl. Assays were run in triplicate using an FL 500 Microplate Fluorescence Reader to determine the fluorescence of each sample. Linear regression was then used to plot the standard curve and extrapolate the concentrations (nmol compound/g tissue) of the unknown for the various treatments. Compound localization within the arterial wall was demonstrated by fluorescence microscopy. The same statistical system used in previous experiments, Friedman's statistic followed by modified Student Neuman Keul's multiple comparison test, was employed for data analysis.

Figure 16:
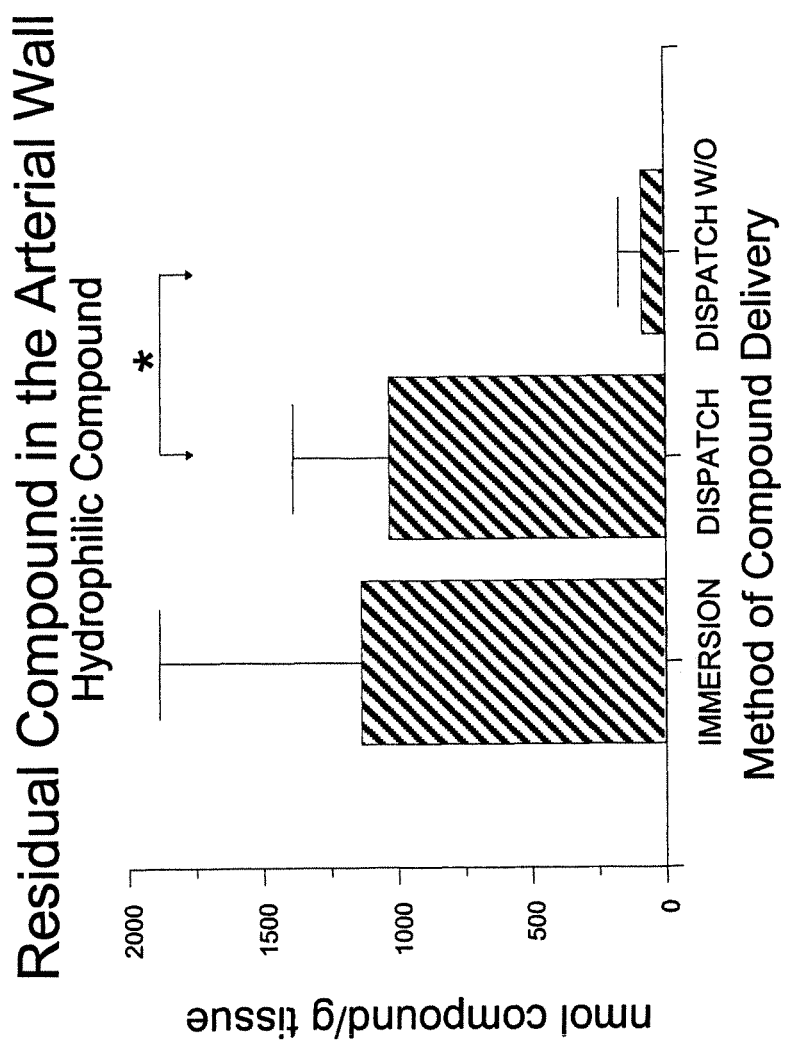
FIG. 16 shows the uptake and retention of a hydrophilic naphthalimide compound in samples of arterial wall based on different delivery methods and after being washed out.
Figure 17:
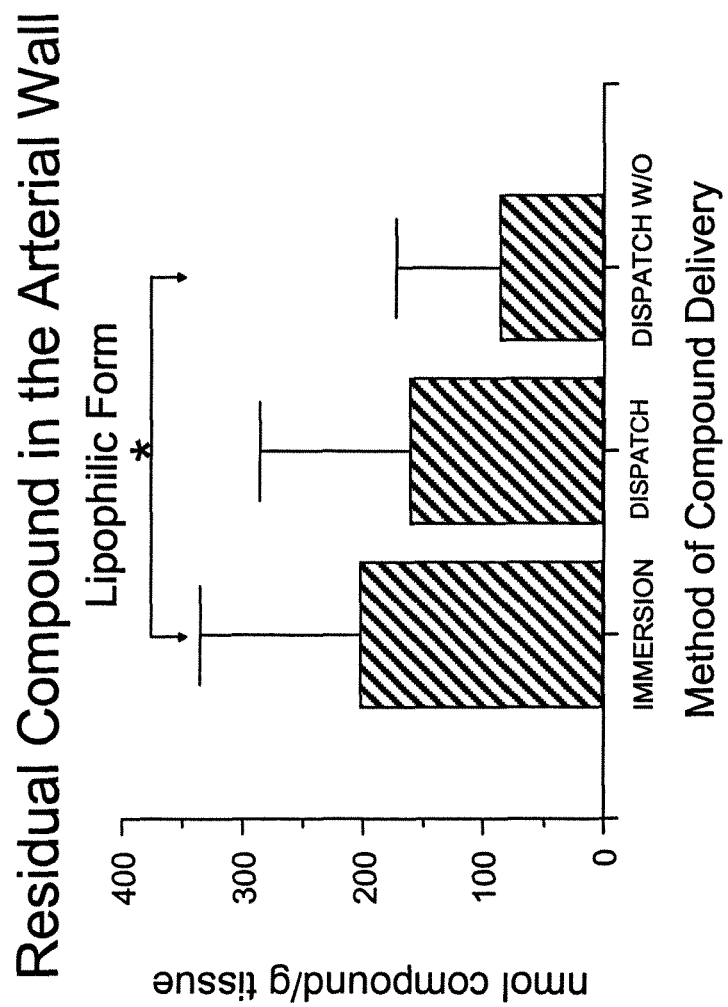
FIG. 17 shows the uptake and retention of a lipophilic naphthalimide compound in samples of arterial wall based on different delivery methods and after being washed out.
Figure 18:
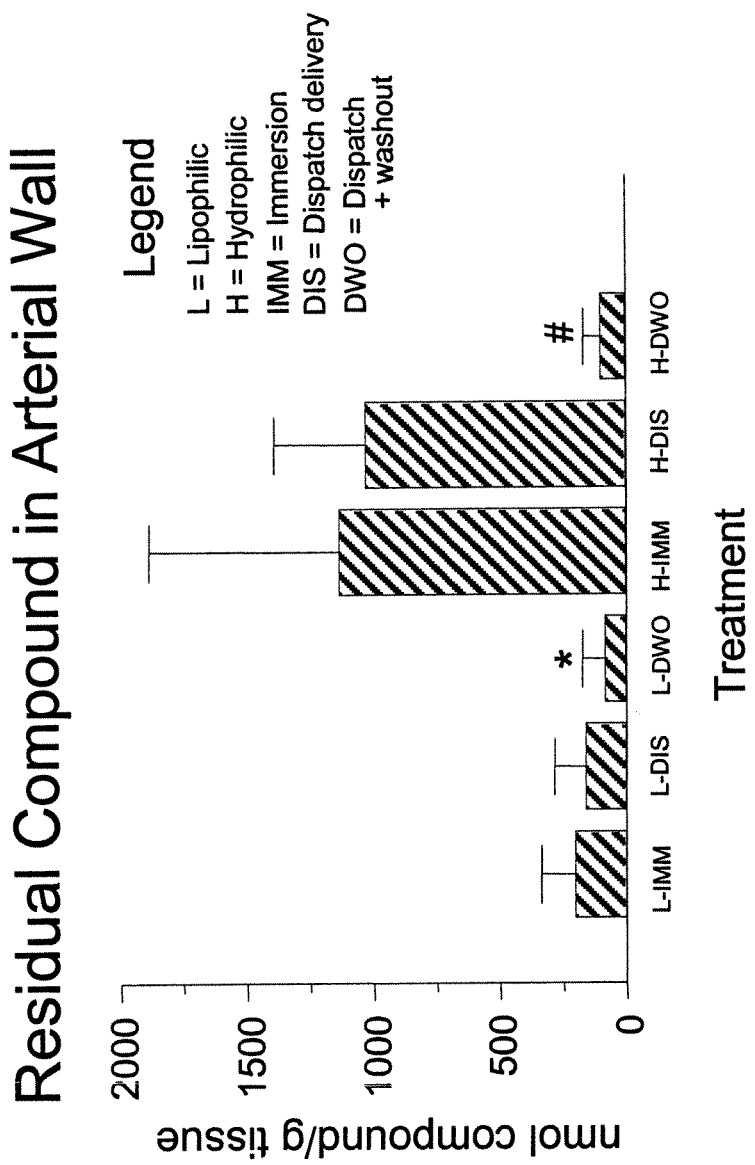
FIG. 18 shows a comparison of the uptake and retention of hydrophilic and lipophilic naphthalimide compounds in samples of arterial wall based on different delivery methods and after being washed out.

The use of the DISPATCH™ catheter resulted in effective luminal delivery of both hydrophilic and lipophilic naphthalimide compounds. FIG. 16 shows the retention of the hydrophilic compound in the arterial wall, FIG. 17 shows the retention of the lipophilic compound in the arterial wall, and FIG. 18 is a comparison of both compounds and treatment methods. Zones of higher intensity of compound were noted in association with the spaced gaps in the delivery coils, but dye concentration was observed along the entire lumen. The total amount of compound delivered was different using the hydrophilic and lipophilic forms, yet was consistent with distributions determined previously using immersion. Using the hydrophilic form, intraluminal delivery resulted in greater compound delivery in four of the five segments tested. In the fifth animal, immersion values were higher than delivery catheter values. In general, values of 1136±749 nmol compound/g tissue was demonstrated for hydrophilic naphthalimide compounds delivered using the DISPATCH™ local drug delivery catheter system.

Since no light exposure was used to bond the tissue during the experiment, washout (W/O) of the compound was substantial for both lipophilic and hydrophilic forms. After 10 minutes of saline perfusion post compound delivery, lipophilic compound levels were 48.2%±38% lower than with intraluminal delivery alone. Hydrophilic levels were 89.2%±8% lower than pre-washout levels. Nevertheless, remaining levels were sufficiently high enough to permit direct observation of tissue fluorescence and color.

The results indicate that intraluminal delivery of the photochemical to the arterial wall components via a DISPATCH™ or similar system to achieve tissue compression stabilization or for drug delivery is a satisfactory system. The hydrophilic compound form is the naphthalimide of choice because it not only localized in regions of the arterial wall but also photochemically linked proteins within the wall.

Example 16

Local Drug Delivery by Photochemical Tethering

In this experiment, in vitro photochemical tethering of heparin to the arterial wall using naphthalimide was analyzed.

Figure 23:
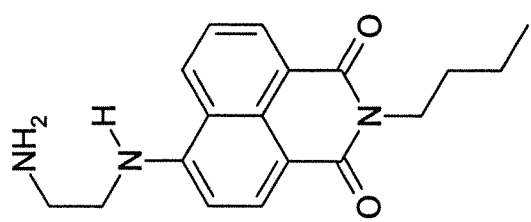
FIG. 23 shows an example of a monomeric hydrophilic 4-amino-1,8-naphthalimide compound.

An example of a naphthalimide compound (having the structure shown in FIG. 23) was bound to enoxaparin (Lovenox®, Aventis Pharmaceuticals, Inc., Bridgewater, N.J.) and biotinylated in a 1:1 ratio using standard biotinylation procedures to provide a means of marking the heparin for histological localization. The heparin was bound to the naphthalimide as shown in FIG. 3 by covalent attachment to the naphthalimide compound.

This modified heparin compound was then applied to the luminal surface of excised swine coronary arteries. Experimental sections were irradiated with 800 mW/cm$^2$ of 400-500 nm blue light for 5 minutes. Control sections received light without the compound, the compound without light, or neither the compound nor light. All sections then underwent sequential washings to remove the unattached heparin. Comparisons were made based on the coloration of the sections. Specimens receiving both the heparin/naphthalimide compound and the photoactivating blue light irradiation showed strong staining along the luminal surface and, to a lesser degree, throughout the arterial wall. Thus, definitive photochemical attachment of heparin to the wall was shown with localization primarily on the luminal surface, but with substantial penetration and bonding to the media as well. Negative controls failed to demonstrate the typical brown staining indicating residual heparin presence. All specimens showed some artifactual red staining within the intima, and the yellowish appearance of the compound/no light specimen indicated some residual naphthalimide presence after washings.

Light activation of the naphthalimide, as indicated previously, results in cleavage of the amine group in the four position, resulting in the loss of its typical yellow coloration. The appearance of the localized biotinylation product and the lack of yellow color in the arterial wall of the experimental group (naphthalimide-modified heparin and light) provided additional evidence of successful bonding within tissue. The lack of yellow indicated successful photochemical modification of the naphthalimide, as breaking of the bond in the 4-amino position results in loss of the color and frees both the naphthalimide ring and the tethered heparin to bind to the tissue.

The results indicate that successful photochemical tethering of a clinically useful pharmacological agent, heparin, to arterial wall tissue with a 4-amino-1,8-naphthalimide was achieved.

Example 17

Synthesis of Sunscreen-Modified Chitosan

To prepare phenylbenzimidazole sulfonyl chloride, 0.5 g of phenylbenzimidazole sulfonic acid (274 g/mole) (1.8 mmoles) was added to 50 ml of dry dioxane and stirred under reflux until dissolved. 0.21 g of thionyl chloride (3.6 mmoles) was added to the reaction and the mixture refluxed for 30 minutes. After 30 minutes the reflux condenser was replaced by a still head and the solvent was removed by distillation to a final volume of 5 ml of dioxane still in the flask.

The phenylbenzimidazole sulfonyl chloride was then added dropwise to 1 gram of chitosan that had been dissolved in 20 ml of 10% acetic acid. This mixture was stirred for one hour, after which the pH was raised to 8 by the dropwise addition of 1 M KOH with stirring. The mixture was allow to react for three hours after which the modified chitosan was collected by centrifugation, redissolved in dilute acetic acid, and dialyzed against PBS.

Example 18

Tethering of Sunscreen-Modified Biomolecule

To test the adherence of the sunscreen to the skin and the penetration of the sunscreen into the skin, the skin of 6 female, Sprague Dawley hairless rats were harvested. The naphthalimide (50 mg of Bradsyl in 1 ml of acetone) was added at the same time as the phenylbenzimidazole sulfonyl chloride of Example 17 producing a sunscreen and naphthalimide modified chitosan. The sunscreen prepared above was applied to 2×2 cm skin samples, allowed to dry and then washed to simulate swimming. A 40 minute dry and 20 minute wash constituted one cycle. Different samples underwent up to six dry/wash cycles. The glove tips used to apply the sunscreen, the water washes, and an extraction of the sunscreen off skin with dilute lactic acid were analyzed using the fluorescence of the tracer molecule to determine the amount of sunscreen that remained adhered to the skin.

The penetration study also utilized the fluorescent tracer molecule attached to the sunscreen. After various dry/wash cycles, the samples were preserved and processed for fluorescent microscopy analysis. The fluorescent tracer demonstrated the degree of penetration of the sunscreen into the skin. The intensity of the fluorescent tracer molecule was also evaluated to determine how much sunscreen was adhered to the skin.

Figure 24:
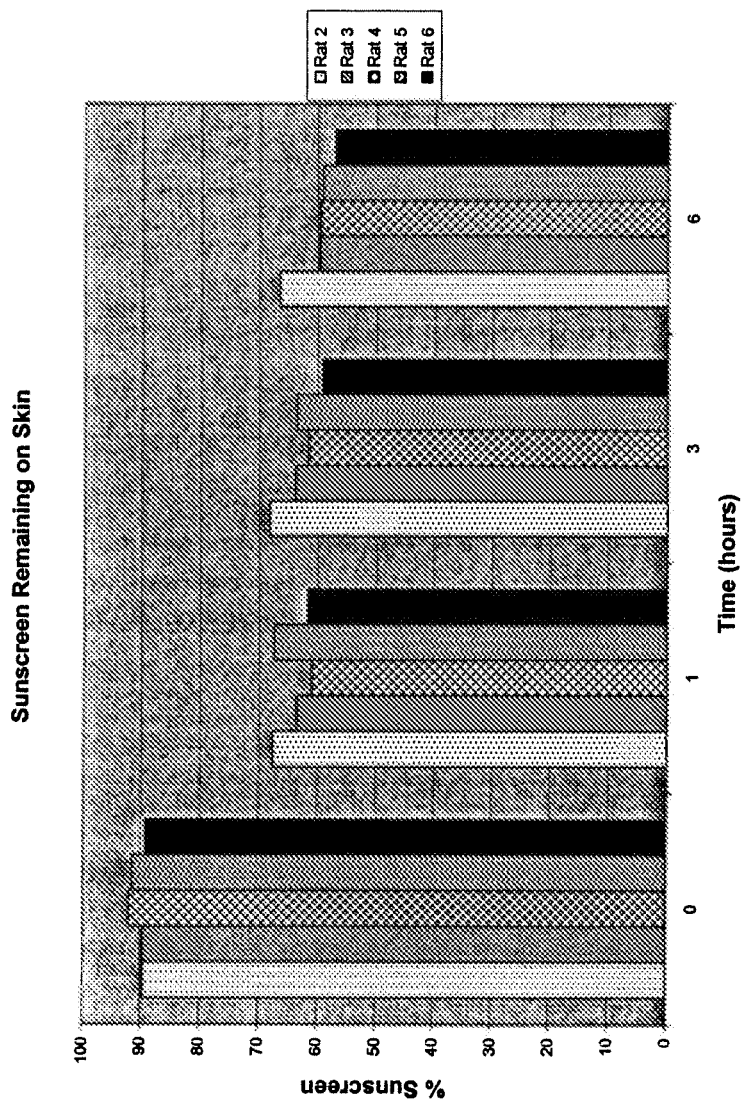
FIG. 24 shows the adherence of a sunscreen-modified biomolecule to skin over time.

As shown in FIG. 24, the results of the study conclude that after a series of six dry/wash cycles approximately 60% of the sunscreen remains tethered to the skin. The majority of the remaining 40% of the sunscreen was lost on the glove tip during application or in the first water wash. The fluorescence microscopy verified that the sunscreen was only adhering to the epidermal surface and not penetrating into the skin.

REFERENCES CITED

The following U.S. Patent documents and publications are hereby incorporated by reference.

U.S. Patents

| U.S. Pat. No. | Issued to: |
| --- | --- |
| 5,235,045 | Lewis, et al. |
| 5,565,551 | Lewis, et al. |
| 5,766,600 | Lewis, et al. |
| 5,917,045 | Lewis, et al. |
| 6,410,505 | Lewis, et al. |

Other Publications

LeVeen, R., Wolf, G., Villanueva, T. New rabbit atherosclerosis model for the investigation of transluminal angioplasty. *Invest Radiol*, vol. 17, pp. 470-75, 1982.

What is claimed is:

1. A method for preserving an expanded luminal diameter of a blood vessel at a treatment site, comprising:
    expanding a vessel lumen having a first diameter, which is smaller than a normal lumen diameter for the vessel at a location adjacent to the treatment site, to a second diameter which is equal to or greater than the normal lumen diameter;
    infusing an effective amount of a 4-amino-1,8-naphthalimide compound into the lumen; and
    activating the 4-amino-1,8-naphthalimide compound with a sufficient amount of an activating agent to initiate cross-linking.

2. The method of claim 1, wherein the second lumen diameter is maintained during the activating step.

3. The method of claim 1, wherein the second diameter of the lumen comprises a diameter which exceeds the normal diameter by up to thirty percent.

4. The method of claim 1, wherein the lumen diameter is expanded by balloon angioplasty.

5. The method of claim 1, wherein the expanding step is performed at least one of prior to, during, and subsequent to the infusing step.

6. The method of claim 1, wherein the 4-amino-1,8-naphthalimide compound has a structure selected from the group consisting of:

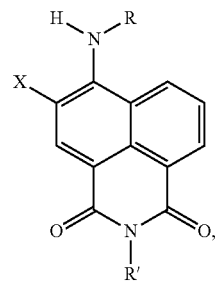 (I)

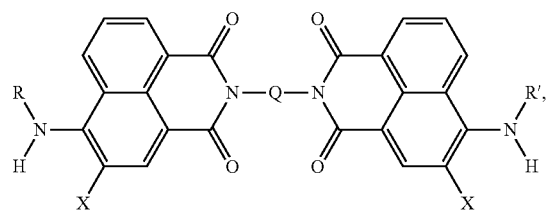 (II)

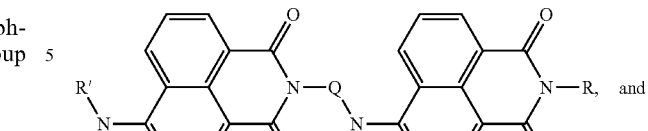 (III)

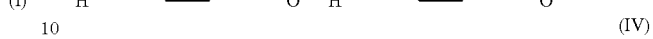

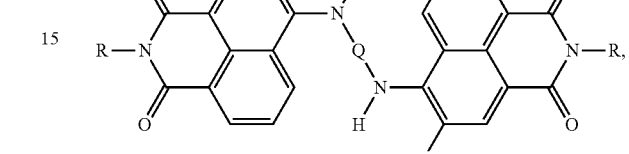 (IV)

wherein R, R', and Q are each independently selected from the group consisting of straight-chain and branched chain alkyl groups having from 2 to 200 carbons; and wherein X is hydrogen.

7. The method of claim 1, wherein the activating agent is selected from radiated energy, electromagnetic energy, laser, electric current, electrons, thermal neutrons, and chemicals.

* * * * *